(12) United States Patent
Smith

(10) Patent No.: US 9,188,517 B2
(45) Date of Patent: Nov. 17, 2015

(54) APPARATUS, SYSTEMS, AND METHODS FOR SAMPLING AND CONDITIONING A FLUID

(71) Applicant: Horiba Instruments, Inc., Irvine, CA (US)

(72) Inventor: Stevie Horton Smith, Seabrook, TX (US)

(73) Assignee: HORIBA Instruments Incorporated, Irvine, CA (US)

(*) Notice: Subject to any disclaimer, the term of this patent is extended or adjusted under 35 U.S.C. 154(b) by 0 days.

(21) Appl. No.: 13/902,090

(22) Filed: May 24, 2013

(65) Prior Publication Data

US 2013/0247768 A1    Sep. 26, 2013

Related U.S. Application Data

(60) Division of application No. 13/528,733, filed on Jun. 20, 2012, now Pat. No. 8,475,565, which is a continuation of application No. 12/700,317, filed on Feb. 4, 2010, now Pat. No. 8,211,210.

(51) Int. Cl.
| | |
|---|---|
| *B01D 46/46* | (2006.01) |
| *G01N 1/34* | (2006.01) |
| *B01D 45/08* | (2006.01) |
| *B01D 46/00* | (2006.01) |
| *B01D 45/14* | (2006.01) |
| *B01D 45/16* | (2006.01) |
| *G01N 1/22* | (2006.01) |
| *G01N 33/22* | (2006.01) |

(52) U.S. Cl.
CPC *G01N 1/34* (2013.01); *B01D 45/08* (2013.01); *B01D 45/14* (2013.01); *B01D 45/16* (2013.01); *B01D 46/0086* (2013.01); *G01N 1/2247* (2013.01); *G01N 33/225* (2013.01)

(58) Field of Classification Search
CPC .... B01D 45/08; B01D 46/0086; B01D 45/14; B01D 45/16
USPC ........ 55/442–446, 434.1, 400, 402, 403–408, 55/434.2, 434.3; 96/413, 417, 16, 407, 96/420; 95/14, 17, 16; 73/863.21, 864.81, 73/31.07
See application file for complete search history.

(56) References Cited

U.S. PATENT DOCUMENTS

| | | | |
|---|---|---|---|
| 1,511,854 A | 10/1924 | Waters | |
| 1,779,023 A | * 10/1930 | Waters | ............................ 55/446 |
| 3,135,684 A | 6/1964 | Ackeret et al. | |
| 4,461,183 A | 7/1984 | Wedding | |
| 5,229,014 A | 7/1993 | Collins | |

(Continued)

OTHER PUBLICATIONS

PCT/US2011/022824 International Search Report and Written Opinion, Sep. 29, 2011, 10 pgs.

*Primary Examiner* — Dung H Bui
(74) *Attorney, Agent, or Firm* — Brooks Kushman P.C.

(57) ABSTRACT

A system of sampling a fluid comprises a fluid separator having a central axis. The fluid separator includes an insulating sleeve. In addition the fluid separator includes a separator assembly coaxially disposed within the sleeve. Further, the fluid separator includes an annulus radially disposed between the sleeve and the separator assembly. The separator assembly includes a conduit, a support rod coaxially disposed within the conduit, and a plurality of separator members coupled to the support rod within the conduit.

19 Claims, 11 Drawing Sheets

(56) References Cited

U.S. PATENT DOCUMENTS

| | | |
|---|---|---|
| 5,837,203 A | 11/1998 | Godec et al. |
| 6,205,869 B1 | 3/2001 | Schadt et al. |
| 6,530,979 B2 | 3/2003 | Firey |
| 6,666,905 B2 | 12/2003 | Page et al. |
| 6,713,112 B1 | 3/2004 | Lucas |
| 6,761,757 B2 | 7/2004 | Welker |
| 7,032,444 B2 | 4/2006 | Breviere et al. |
| 7,081,146 B2 | 7/2006 | Hallgren et al. |
| 7,250,066 B2 | 7/2007 | Seipler |
| 7,513,940 B2 | 4/2009 | Mileham et al. |
| 7,569,094 B2 | 8/2009 | Kane et al. |
| 7,833,303 B1 | 11/2010 | Higgins |
| 7,927,395 B2 | 4/2011 | Szepessy et al. |
| 7,993,425 B2 | 8/2011 | Corattiyil et al. |
| 2003/0226445 A1* | 12/2003 | Titmas ............... 95/288 |
| 2003/0233890 A1 | 12/2003 | Mayeaux |
| 2004/0079236 A1 | 4/2004 | Welker |
| 2005/0087028 A1 | 4/2005 | Widmer |
| 2005/0198932 A1 | 9/2005 | Franzen et al. |
| 2008/0017040 A1 | 1/2008 | Mileham et al. |
| 2009/0266235 A1 | 10/2009 | Kane et al. |
| 2010/0180854 A1 | 7/2010 | Baumann et al. |
| 2011/0185892 A1 | 8/2011 | Smith |

* cited by examiner

APPARATUS, SYSTEMS, AND METHODS FOR SAMPLING AND CONDITIONING A FLUID

CROSS-REFERENCE TO RELATED APPLICATIONS

This application is a divisional of application Ser. No. 13/528,733, filed Jun. 20, 2012, now U.S. Pat. No. 8,475,565, which is a continuation of application Ser. No. 12/700,317, filed Feb. 4, 2010, now U.S. Pat. No. 8,211,210, each of which is incorporated by reference herein in its entirety.

BACKGROUND

1. Field of the Invention

The invention relates generally to analysis of sampled fluids. More particularly, the invention relates to conditioning a sampled hydrocarbon fluid for prior to downstream analysis.

2. Background of the Technology

In the hydrocarbon processing industry, analytical instrumentation is employed at various stages of processing to analyze the chemical composition of the fluids being processed. Typically, the instrumentation analyzes a small sample taken from a hydrocarbon fluid stream undergoing processing. However, prior to introducing the sample to the analytical instrumentation, the sample must be "conditioned" to remove contaminates that may otherwise damage to the instrumentation and/or undesirably skew the analytical results such as product yield results (i.e., desired product volume produced per unit time). In some cases, plant operations may over-react or under-react to the inaccurate results, potentially leading to higher operating cost.

Referring now to FIG. 1, a conventional system 10 for sampling a decoke or green oil fluid stream 15 during hydrocarbon cracking or pyrolysis operations is schematically shown. System 10 includes a fluid conditioner 20 and analytical equipment 30 downstream from conditioner 20. The bulk decoke or green oil (recycle gas) fluid stream 15 is sampled and analyzed to provide insight into the cracking processing. For example, bulk decoke fluid stream 15 may be sampled and analyzed to determine the yield of a desired product (e.g., volume of ethylene or propylene being produced by the cracking process per unit time).

As shown in FIG. 1, a sample 16 is pulled from the bulk decoke fluid stream 15. When sample 16 is initially pulled from the process fluid stream 15, it typically comprises a mixture of a gas 17 to be analyzed and undesirable contaminants 18 such as water and/or relatively heavy hydrocarbons (i.e. C6 and heavier). Contaminants 18 can foul and/or damage downstream fluid transport lines and analytical equipment 30. In addition, contaminants may negatively impact the accuracy of analytical results produced by analytical equipment 30. Consequently, sample 16 is passed through fluid conditioner 20 before being passed to analytical equipment 30. The goal of conditioner 20 is to remove the contaminants 18 from sample 16 prior to analysis. Accordingly, conditioner 20 separates sample 16 into contaminants 18, which are fed back to bulk fluid stream 15, and gas 17, which is passed on to analytical equipment 30 for further analysis. Analytical equipment 30 analyzes gas 17 to determine the yield rate 19 of gas 17, which is communicated to the plant operators. Once analyzed, gas 17 is fed back to bulk fluid stream 15.

Most conventional sample conditioning devices (e.g., conditioner 20) are heat exchangers with manual controls. Such devices allow the relatively hot sample fluid to pass through a cooled pipe that includes a plurality of stacked stainless steel mesh pads. Due to the temperature of the cooled chamber, typically about 60° to 90° F., and the torturous path, defined by the mesh pads, that the sample must navigate through, some of the water and relatively heavy molecular weight components (i.e., components with molecular weights greater than 86) in the sampled fluid will decelerate, form into droplets on the mesh pads, and then fall back down into the hydrocarbon process stream from which they came.

Maintenance of such conventional conditioning devices can be time consuming, labor intensive, and expensive. In particular, most conventional conditioning devices require that the entire device be removed from the pipe string within which it is disposed for service to be performed. In addition, the total surface area provided by the plurality of mesh pads is usually only about 144 in.$^2$, which tends to be more easily fouled. Further, most conventional conditioning devices must be visually inspected and monitored, and manually controlled. In other words, most conventional conditioning devices provide no external insight into the sampling process, the current sample temperature, the status of the conditioner, or the temperature of the cooling air in the conditioner, each of which may allow the plant operators to ascertain whether the analytical data is valid or not.

Accordingly, there remains a need in the art for fluid sampling devices, systems, and methods that offered the potential for improved separation efficiency and insight into the fluid processing being monitored. Such devices and systems would be particularly well received if they could be maintained with reduced effort and expense.

BRIEF SUMMARY OF THE DISCLOSURE

These and other needs in the art are addressed in one embodiment by a fluid sampling system. In an embodiment, the system comprises a fluid separator having a central axis. The separator includes an insulating sleeve. In addition, the separator includes a separator assembly coaxially disposed within the sleeve. Further, the separator includes an annulus radially disposed between the sleeve and the separator assembly. The separator assembly includes a conduit, a support rod coaxially disposed within the conduit, and a plurality of separator members coupled to the support rod within the conduit.

These and other needs in the art are addressed in another embodiment by a system for removing contaminants from a sample fluid. In an embodiment, the system comprises a fluid separator having a central axis and extending axially between an upper end and a lower end. The fluid separator includes an insulating sleeve axially positioned between the upper end and the lower end. In addition, the fluid separator includes a separator assembly coaxially disposed within the sleeve and extending between the upper end and the lower end. The separator assembly includes an inlet and an outlet. Further, the fluid separator includes an annulus radially disposed between the sleeve and the separator assembly. The annulus includes an inlet and an outlet. Still further, the fluid separator includes a cooling device adapted to pump a cooling fluid through the inlet of the annulus. The system also comprises a monitoring and control system coupled to the fluid separator. The monitoring and control system includes a first temperature sensor proximal the outlet of the separator assembly. The first temperature sensor is adapted to measure the temperature of a fluid flowing through the outlet of the separator assembly.

These and other needs in the art are addressed in another embodiment by method. In an embodiment, the method comprises (a) acquiring an unconditioned fluid sample from a bulk fluid stream. In addition, the method comprises (b) providing a separator having a central axis. The separator includes an insulating sleeve, a conduit coaxially disposed within the insulating sleeve, an annulus radially disposed between the insulating sleeve and the conduit, and a plurality of separator members disposed within the conduit. The conduit includes an inlet and an outlet and is radially spaced apart from the insulating sleeve. Further, the annulus has an inlet. Further, the method comprises (c) flowing the unconditioned fluid sample through the inlet of the conduit. Still further, the method comprises (d) flowing a cooling fluid through the inlet of the annulus. Moreover, the method comprises (e) separating a contaminant fluid from the unconditioned fluid sample in the separator assembly to produce a conditioned sample fluid. In addition, the method comprises (f) flowing the conditioned fluid through the outlet of the conduit. Further, the method comprises (g) measuring the temperature of the conditioned sample fluid at the outlet of the conduit. The method also comprises (h) analyzing the conditioned fluid sample to estimate a yield rate for a product in the bulk fluid stream.

Thus, embodiments described herein comprise a combination of features and advantages intended to address various shortcomings associated with certain prior devices, systems, and methods. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the preferred embodiments of the invention, reference will now be made to the accompanying drawings in which.

DETAILED DESCRIPTION OF SOME OF THE PREFERRED EMBODIMENTS

Figure 1:
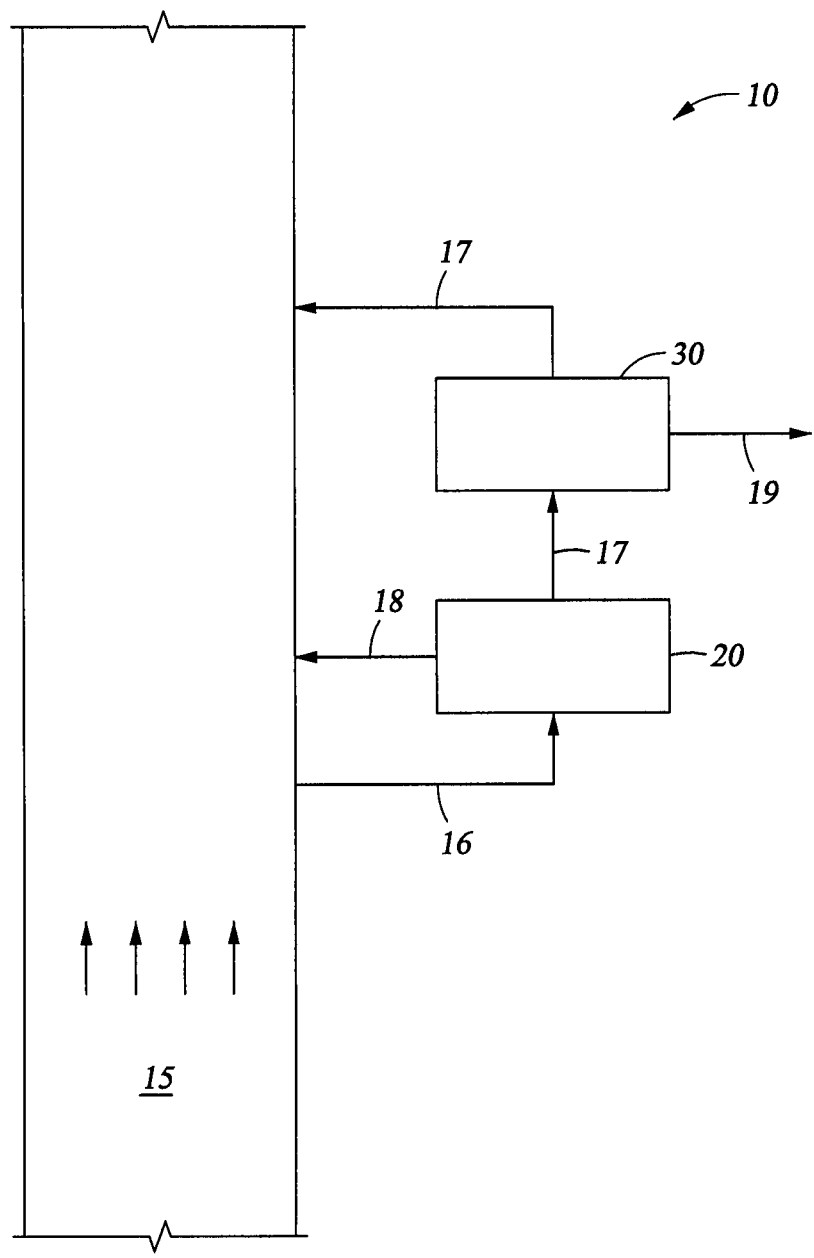
FIG. 1 is a schematic view of a conventional system for sampling a hydrocarbon fluid stream.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis.

Figure 2:
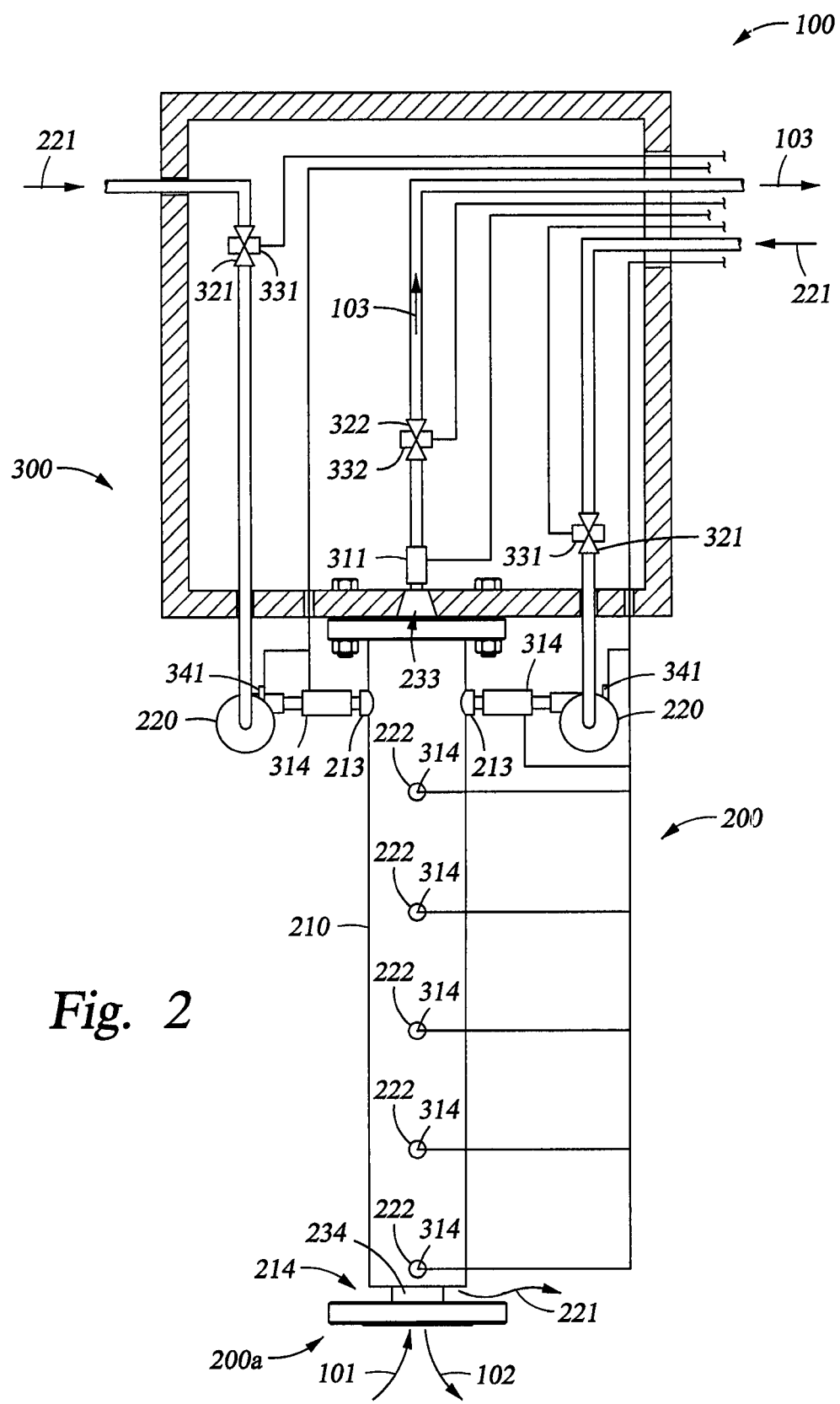
FIG. 2 is a partial cross-sectional schematic view of an embodiment of fluid sampling system in accordance with the principles described herein.

Referring now to FIG. 2, an embodiment of a fluid sampling system 100 is schematically shown. System 100 includes a fluid separator 200 and a sample monitoring and control system 300 coupled to separator 200. In FIG. 2, fluid separator 200 is shown in front view and sample monitoring and control system 300 is shown in a schematic partial cross-sectional view.

In general, fluid separator 200 separates a raw or unconditioned fluid sample 101 taken from a hydrocarbon or chemical processing operation into contaminants 102 and a conditioned fluid sample 103 (i.e., a fluid sample that is substantially free of contaminants that may foul and/or damage downstream equipment), which is passed to downstream analytical equipment for further analysis. In other words, separator 200 conditions the raw fluid sample 101 for subsequent processing and analysis. Accordingly, separator 200 may also be referred to as a "fluid conditioner" or "fluid conditioning device." Sample monitoring and control module 300 measures multiple predetermined parameters associated with the sample separation process and controls the sample separation process within separator 200. As will be described in more detail below, module 300 may adjust the sample separating process within separator 200 automatically based on the measured parameters (i.e., without human intervention) and/or in response to input from a remote operator. In practice, a plurality of systems 100 may be employed in a chemical or hydrocarbon processing operation to sample fluid and condition the sampled fluids at different stages or locations along the processing operations.

In the embodiments described herein, system 100 is employed to aid in the sampling and analysis of a decoke fluid sample from a hydrocarbon cracking operation to determine the ethylene and/or propylene yields during the cracking operations. Thus, raw fluid sample 101 comprises an unconditioned decoke fluid sample taken from a bulk decoke fluid stream flowing through the hydrocarbon cracking equipment. The unconditioned decoke fluid sample 101 typically comprises a mixture of contaminants such as water, relatively heavy hydrocarbons (i.e., hydrocarbon molecules having six or more carbon atoms), small quantities of particulate matter, which can foul and/or damage downstream sampling equipment, and the relatively light hydrocarbons (i.e., hydrocarbons molecules having five or less carbon atoms) such as ethylene, propylene, methane, ethane, and propane. Accordingly, contaminants 102 comprise water, relatively heavy hydrocarbons, and particulate matter; conditioned fluid sample 103 comprises a mixture of the relatively light hydrocarbons as well as small amounts of other non-contaminating fluids that do not foul or damage downstream hardware. Thus, fluid separator 200 receives unconditioned decoke fluid sample (i.e., unconditioned fluid sample 101), separates water, relatively heavy hydrocarbons, and particulate matter (i.e., contaminants 102) from the unconditioned decoke fluid sample, and outputs a mixture of the relatively light hydrocarbons and small amount of other non-contaminating fluids (i.e., conditioned fluid sample 103). Once separated, contaminants 102 are allowed to flow back into the bulk decoke fluid stream. Due to the elevated temperature of the bulk decoke fluid stream, the unconditioned fluid sample 101 is typically a relatively hot gas with some suspended particulate matter. As will be described in more detail below, during conditioning with separator 200, unconditioned fluid sample 101 is cooled, and as a result, gaseous contaminants 102 such as water and relatively heavy hydrocarbons phase change to liquid droplets that coalesce within separator 200. Although unconditioned fluid sample 101 is cooled and gaseous contaminants 102 separate out in liquid form, conditioned fluid sample 103 remains a gas, albeit at a lower temperature than the unconditioned fluid sample 101. Following conditioning with separator 200, the conditioned fluid sample 103 may then be passed downstream to analytical equipment to determine the ethylene and/or propylene yields during the cracking operation. By removing contaminants 102 from the unconditioned fluid sample 101 to produced conditioned sample 103, separator 200 offers the potential to reduce fouling and/or damage to downstream hardware by contaminants 102.

Figure 3:
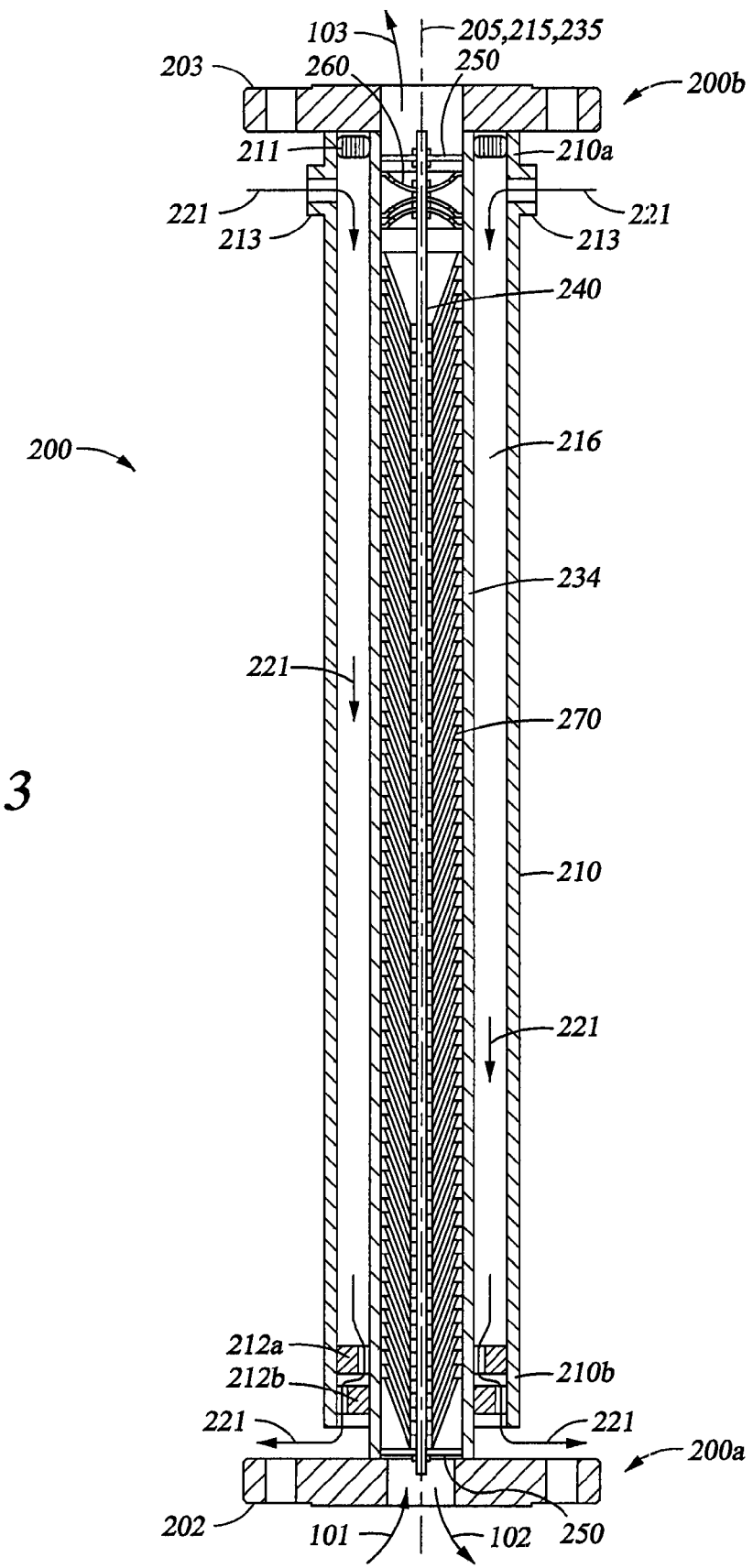
FIG. 3 is a partial cross-sectional view of the fluid separator of FIG. 2.

Referring now to FIGS. 2 and 3, fluid separator 200 has a central or longitudinal axis 205 and extends axially between a first or lower end 200a and a second or upper end 200b. In this embodiment, each end 200a, b comprises a mounting flange 202, 203, respectively. Lower flange 202 couples fluid separator 200 to other device(s) and/or fluid conduit(s) positioned upstream of separator 200 relative to the flow of unconditioned fluid sample 101, and upper flange 203 couples fluid separator 200 to other device(s) and fluid conduit(s) positioned downstream of fluid separator 200 relative to the flow of unconditioned fluid sample 101. In addition, fluid separator 200 includes a radially outer insulating sleeve 210 and a radially inner separator assembly 230 coaxially disposed within sleeve 210.

Figure 4:
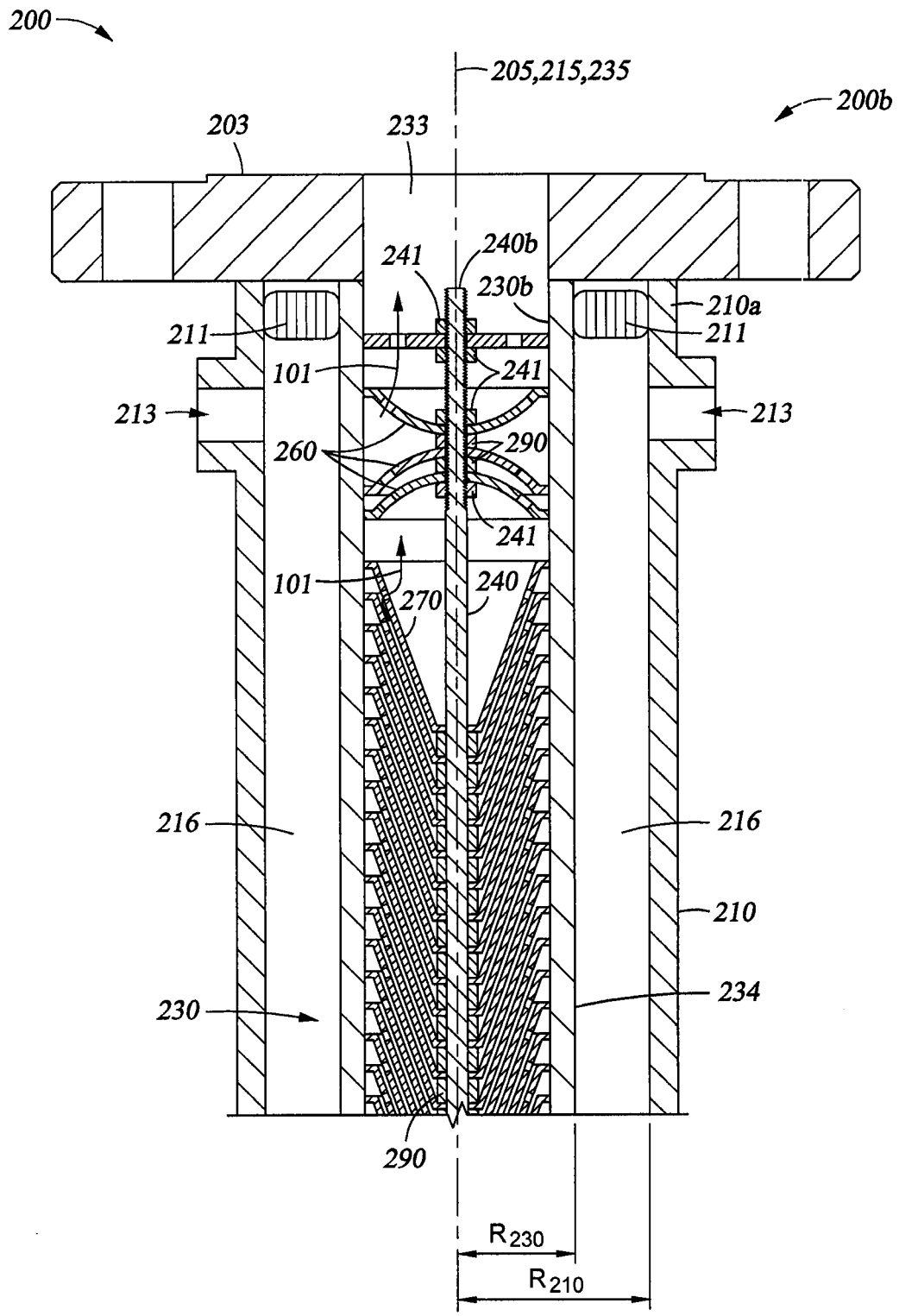
FIG. 4 is a cross-sectional view of the upper end of the fluid separator of FIG. 2.
Figure 5:
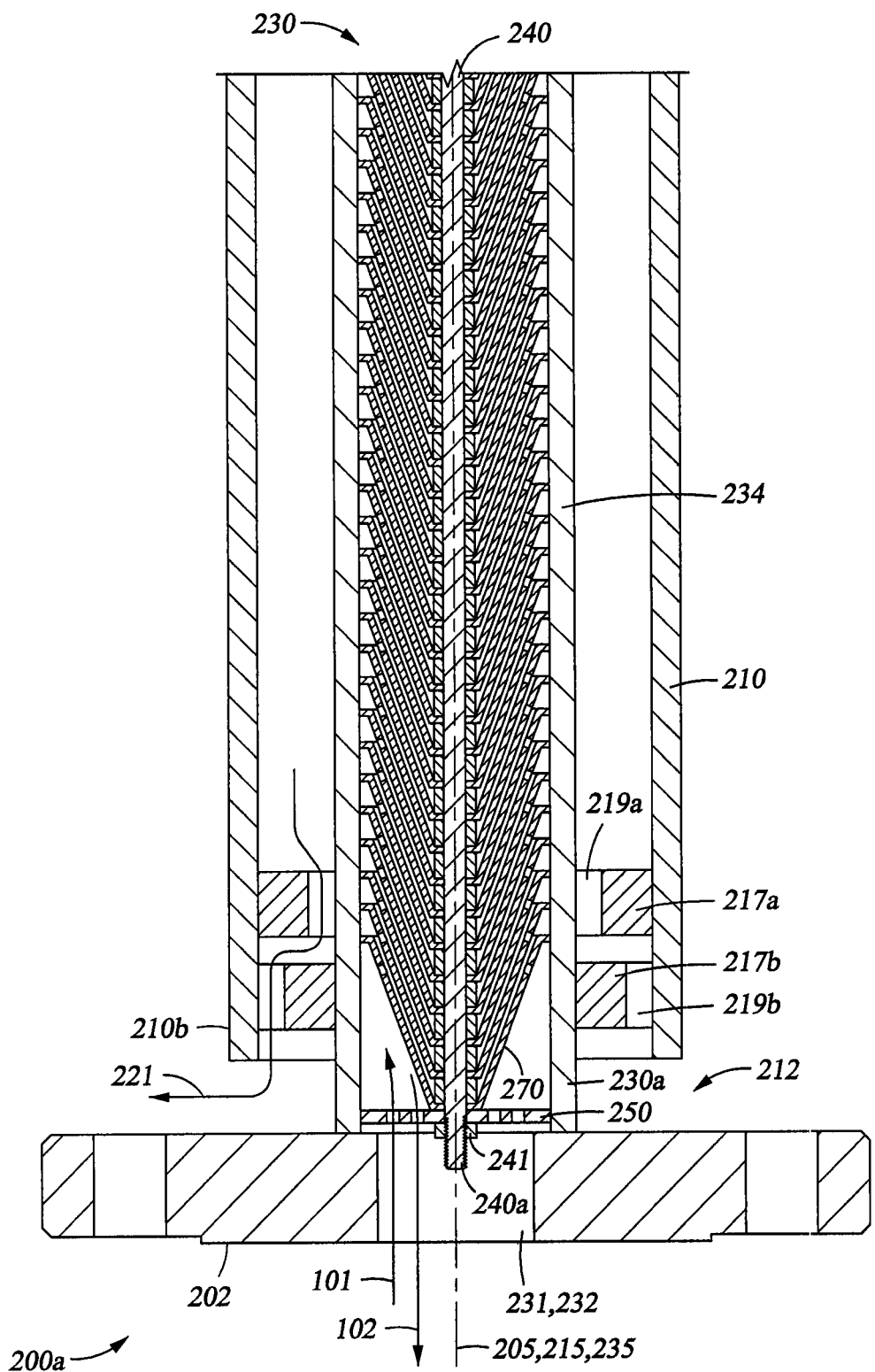
FIG. 5 is a cross-sectional view of the lower end of the fluid separator of FIG. 2.

Referring now to FIGS. 3-5, insulating sleeve 210 has a central or longitudinal axis 215 coincident with axis 205 and extends axially between a first or upper end 210a proximal upper flange 203 and a second or lower end 210b proximal lower flange 202. In this embodiment, insulating sleeve 210 is a tubular having a cylindrical cross-section in a plane perpendicular to axis 215, however, in general, the insulating sleeve (e.g., sleeve 210) may have any suitable cross-sectional shape (e.g., square, rectangular, triangular, oval, etc.).

As best shown in FIGS. 3 and 4, sleeve 210 is axially positioned between flanges 202, 203 and is coaxially disposed about assembly 230. Sleeve 210 has an inner radius $R_{210}$ that is greater than the outer radius $R_{230}$ of separator assembly 230 (FIG. 4). Thus, sleeve 210 is radially spaced from assembly 230, thereby defining an insulating annulus or chamber 216 extending radially between sleeve 210 and assembly 230 and extending axially between ends 210a, 210b. In addition, sleeve 210 includes a pair of circumferentially spaced openings 213 disposed at the same axial position proximal upper end 210a. In this embodiment, openings 213 are uniformly spaced about 180° apart about axis 215. Each opening 213 extends radially through sleeve 210 to insulating chamber 216, and thus, each opening 213 is in fluid communication with insulating chamber 216. As will be described in more detail below, during operation of fluid separator 200, fluid flows through openings 213 and into insulating chamber 216. Consequently, each opening 213 may also be referred to herein as an inlet 213 of annulus 216.

An annular seal 211 is disposed within annulus 216 proximal upper end 210a and axially above inlets 213. Seal 211 extends radially between insulating sleeve 210 and separator assembly 230, and sealingly engages the cylindrical inner surface of insulating sleeve 210 and the outer cylindrical surface of separator assembly 230. Seal 211 restricts and/or prevents fluid within annulus 216 from flowing axially upward to the interface between upper end 210a and upper flange 203.

Figure 14:
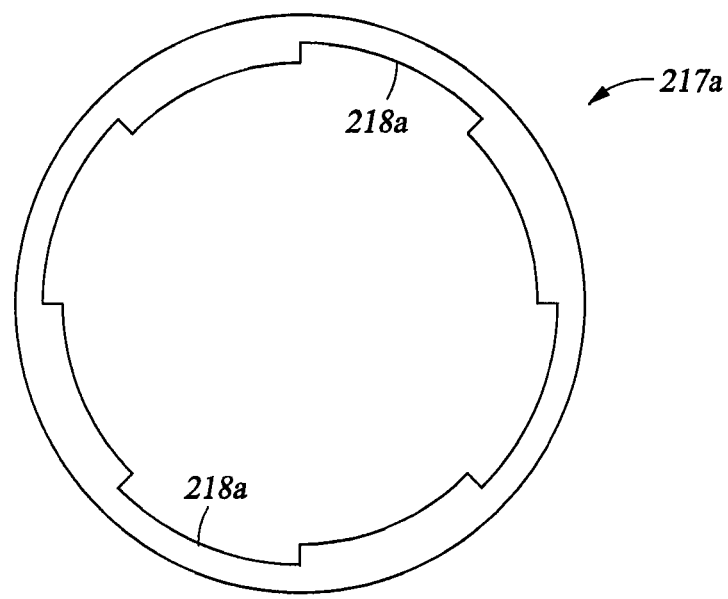
FIG. 14 is an enlarged top view of the upper gasket of FIG. 5.
Figure 15:
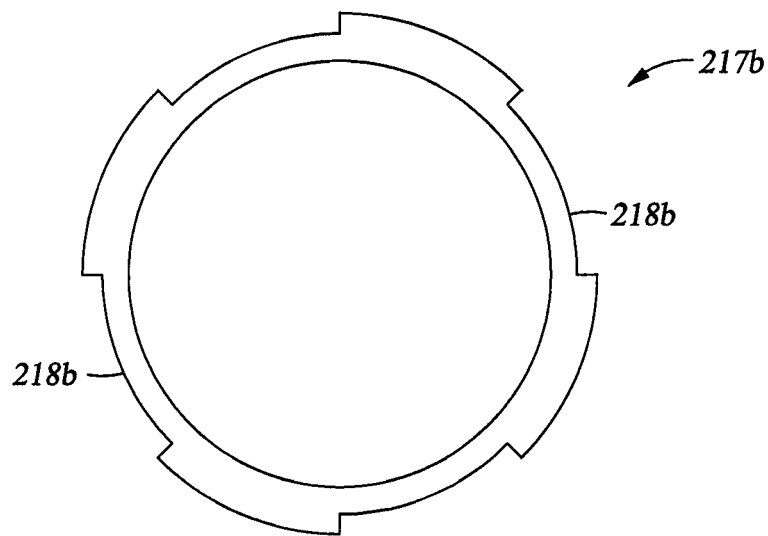
FIG. 15 is an enlarged top view of the lower gasket of FIG. 5.

As best shown in FIGS. 3 and 5, lower end 210b of sleeve 210 does not extend axially to or engage lower flange 202. Rather, lower end 210b of sleeve 210 is axially spaced apart from flange 202, thereby defining an annular gap 214. An upper or first annular gasket 217a and a second or lower annular gasket 217b are disposed in insulating chamber 216 proximal lower end 210b and axially above gap 214. Lower gasket 217b is axially spaced below upper gasket 217a, and each annular gasket 217a, b extends radially between insulating sleeve 210 and separator assembly 230. As best shown in FIGS. 5, 14, and 15, the radially outer cylindrical surface of upper gasket 217a sealingly engages the radially inner cylindrical surface of sleeve 210, and the radially inner cylindrical surface of lower gasket 217b sealingly engages the radially outer cylindrical surface of separator assembly 230. However, the radially inner surface of upper gasket 217a includes a plurality of circumferentially spaced recesses 218a, each recess 218a extending axially through gasket 217a from the upper surface of gasket 217a to the lower surface of gasket 217a. Further, the radially outer surface of lower gasket 217b includes a plurality of circumferentially spaced recesses 218b, each recess 218b extend axially through gasket 217b from the upper surface of gasket 217a to the lower surface of gasket 217b. Recesses 218a, b define axial flow passages 219a, b, respectively, in gaskets 217a, b, respectively. Flow passages 219a, b are in fluid communication with insulating chamber 216 and annular gap 214. Thus, gap 214 is in fluid communication with insulating chamber 216 via flow passages 219a, b. As will be described in more detail below, during operation of fluid separator 200, fluid flows from insulating chamber 216, through flow passages, 219a, b and radially outward through gap 214. Consequently, annular gap 214 may also be referred to herein as an outlet 214 of annulus 216. Gasket 217a is preferably oriented such that recesses 218a are angularly offset from recesses 218b in order to create a more tortuous path for fluid flowing from insulating chamber 216 to outlet 214 and a slight backpressure within insulating chamber 216.

In general, seal 211 and gaskets 217a, b may comprise any suitable material(s) capable of sealingly engaging insulating sleeve 210 and/or separator assembly 230. However, seal 211 and gaskets 217a, b preferably comprises a resilient and durable material such as neoprene or rubber. In this embodiment, seal 211 and each gasket 217a, b is a neoprene gasket.

Referring again to FIGS. 2 and 3, each inlet 213 is in fluid communication with a cooling device 220 that pumps a cooling medium or fluid 221, typically cold air, through each inlet 213 and into insulating chamber 216. In general, each cooling device 310 may comprise any suitable device capable of cooling a fluid and pumping the cooling fluid 221 through insulating chamber 216 including, without limitation, a thermoelectric cooling device. Examples of a suitable devices for the cooling device (e.g., cooling device 310) include a 2,800 BTU Vortex Cooler™ available from ITW Air Management Co. of Cincinnati, Ohio, and Vortex Koolers available from Rittal Corporation of Urbana, Ohio.

As will be described in more detail below, during operation of fluid separator 200, cooling devices 220 pump cooling fluid 221 through inlets 213 into insulating chamber 216. The cooling fluid 221 flows axially downward through insulating chamber 216 and flow passages 219a, b, and then flows radially outward through outlet 214, thereby exiting fluid separator 200. In this embodiment, upon exiting outlet 214, the cooling fluid 221 is exhausted to the atmosphere. However, in other embodiments, the cooling fluid (e.g., cooling fluid 221) may be returned to the cooling devices (e.g., cooling devices 220), re-cooled, and then recirculated back through the insulating chamber (e.g., insulating chamber 216). Depending on the desired temperature of the cooling fluid 221, one or both cooling devices 220 may be operated. For example, during the summer, operation of both cooling devices 221 may be necessary to achieve the desired temperature for the cooling fluid 221 flowing through insulating chamber 216. However, during the winter, operation of only one cooling device 220 may be necessary to achieve the desired temperature for the cooling fluid 221 flowing through insulating chamber 216.

As best shown in FIG. 1, sleeve 210 also includes a plurality of axially spaced sensor ports 222, each port 222 extending radially through sleeve 210 from the radially outer surface of sleeve 210 to the radially inner surface of sleeve 210 and insulating chamber 216. A temperature sensor 314 is positioned in each sensor port 222. In general, temperature sensors 314 measure the temperature of the cooling fluid 221 at various points along its flow path through fluid separator 200. The axially lowermost port 222 is positioned adjacent outlet 214, and thus, temperature sensor 314 in the axially lowermost port 222 measures the temperature of cooling fluid 221 at outlet 214. Accordingly, temperature sensor 314 in the axially lowermost port 222 may be referred to as the cooling fluid outlet temperature sensor 314. Moreover, one temperature sensor 314 is positioned at each inlet 213 to measure the temperature of cooling fluid 221 at each inlet 213. The temperature sensors 314 positioned at inlets 213 may be referred to as the cooling fluid inlet temperature sensors 314.

In general, sleeve 210 may comprise any suitable material(s) including, without limitation, metals and metal alloys (e.g., aluminum, steel, etc.), non-metal(s) (e.g., ceramic, polymer, etc.), composite (e.g., carbon fiber and epoxy composite), or combinations thereof. However, sleeve 210 preferably comprise a durable material suitable for use in chemical and hydrocarbon processing environments. In this embodiment, sleeve 210 comprises two layers, a radially inner layer comprising fiberglass pre-formed insulation and a radially outer protective layer comprising carbon fiber reinforced polymer (e.g., epoxy, polyester, vinyl ester, or nylon). The radially inner layer limits heat transfer radially across sleeve 210, while the radially outer layer provides a relatively hard shell that protects the radially inner insulation during maintenance and collateral activities.

Referring again to FIGS. 3-6, separator assembly 230 has a central or longitudinal axis 235 and extends between a first or lower end 230a at lower flange 202 and a second or upper end 230b at upper flange 203. As will be described in more detail below, lower end 230a defines an inlet 231 for unconditioned sample fluid 101 and an outlet 232 for contaminants 102, and upper end 230b defines an outlet 233 for conditioned sample fluid 103. In other words, lower end 230a functions as both inlet 231 and outlet 232, whereas upper end 230b functions solely as outlet 233.

Separator assembly 230 includes a radially outer tubular fluid conduit 234, a radially inner support rod 240 coaxially disposed within conduit 234, a plurality of plates 250, a plurality of baffles 260, a plurality of separating members 270, and a plurality of spacers 290. In this embodiment, separator assembly 230 includes two plates 250—one upper plate 250 (FIG. 4) axially positioned at upper end 230b and one lower plate 250 (FIG. 5) axially positioned at lower end 230a. As best shown in FIGS. 3 and 4, baffles 260 are axially positioned proximal upper end 230b, and separating members 270 are axially positioned between baffles 260 and lower plate 250. Each plate 250, baffle 260, and separator member 270 extends radially between support rod 240 and conduit 234. Further, one spacer 290 is axially positioned between each pair of axially adjacent baffles 260 and each pair of axially adjacent separating members 270. Each spacer 290 comprises a washer or donut having a central throughbore that slidingly receives support rod 240. To achieve the desired axial spacing of baffles 260 and separating members 270, each spacer 290 preferably has an axial height ranging from 1/32 in. to 1/4 in.

Referring still to FIGS. 3-6, conduit 234 has a central axis coincident with axes 205, 215, 235 and extends axially between ends 230a, b and flanges 202, 203. In this embodiment, conduit 234 is integral with flange 202, 203 at each end 230a, b, respectively. For example, flanges 202, 203 may be molded or cast as part of conduit 234, machined from the same material as conduit 234, or manufacture separate from conduit 234 and then welded to the ends of conduit 234. Conduit 234 is an elongate cylindrical tubular or pipe that prevents fluid communication between the fluids flowing within separator assembly 230 (e.g., unconditioned sample fluid 101, contaminants 102, and conditioned sample fluid 103) and the cooling fluid 221 flowing through insulating chamber 216.

Figure 6:
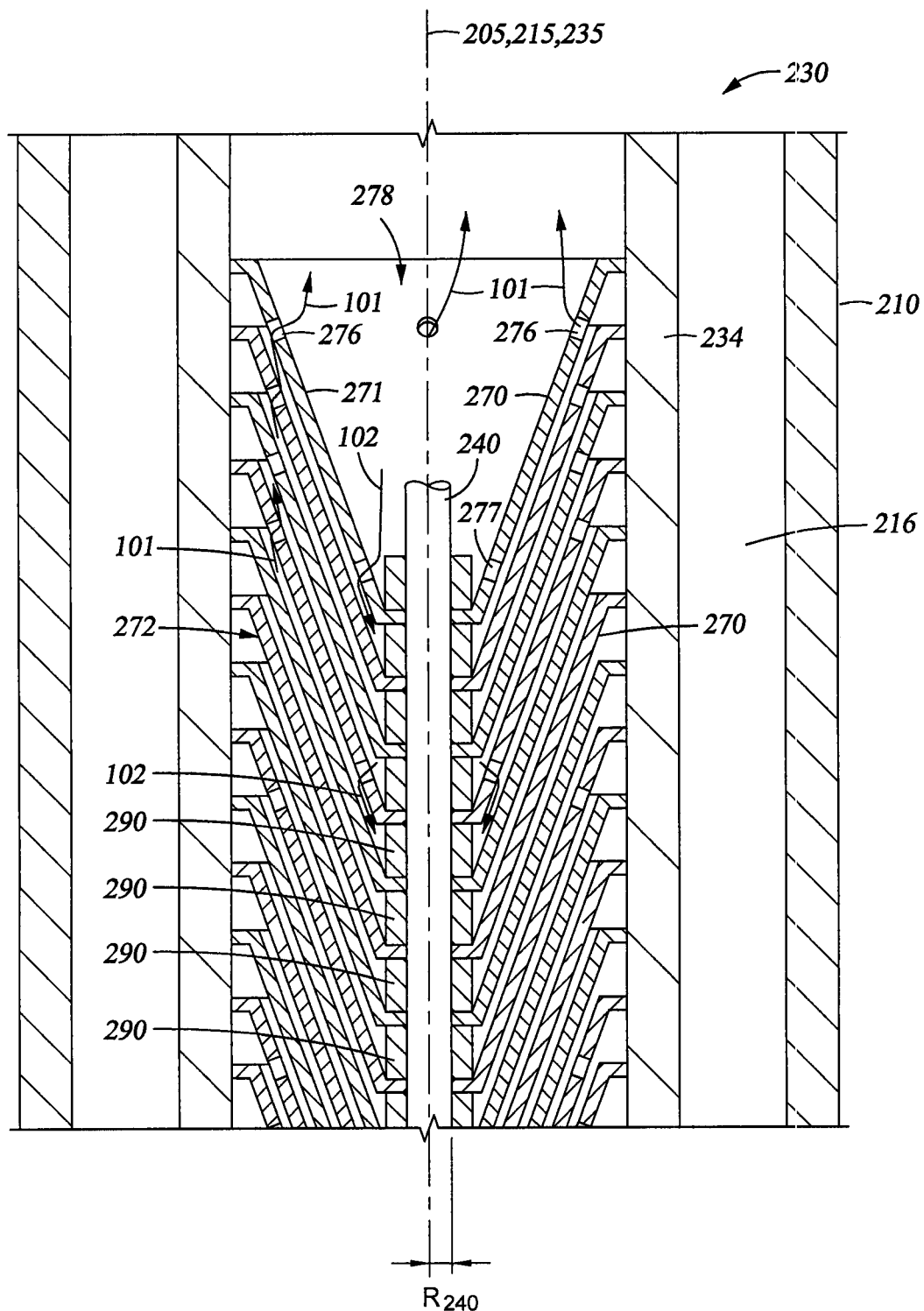
FIG. 6 is a cross-sectional view of an intermediate portion of the fluid separator of FIG. 2.

Support rod 240 is an elongate generally cylindrical rod coaxially disposed within conduit 234, and thus, similar to conduit 234, support rod 240 has a central axis coincident with axes 205, 215, 235. In addition, support rod 240 extends axially between a first or lower end 240a at end 230a and a second or upper end 240b at end 230b. As will be described in more detail below, rod 240 extends through a central throughbore in each plate 250, baffle 260, separator member 270, and spacer 290, thereby radially aligning plates 250, baffles 260, separating members 270, and spacers 290. As best shown in FIG. 6, support rod 240 has an outer radius $R_{240}$ that is preferably between 1/16 in. and 3/16 in. In this embodiment, radius $R_{240}$ is 1/8 in.

Rod 240 comprises external threads at both ends 240a, b, which engage mating nuts 241. In general, nuts 241 maintain the axial position of plates 250, baffles 260, separating members 270, and spacers 290 relative to support rod 240. In other words, nuts 241 restrict axial movement of plates 250, baffles 260, separating members 270, and spacers 290 relative to support rod 240. Specifically, as best shown in FIG. 5, one nut 241 threaded onto lower end 240a of support rod 230 axially abuts and engages lower plate 250. Nut 241 at lower end 240a restricts and/or prevents lower plate 250, separating members 270, and spacers 290 axially positioned between adjacent separating members 270 from sliding off support rod 240. Still further, as best shown in FIG. 4, four nuts 241 are provided proximal upper end 240b to maintain the axial position of baffles 260 and upper plate 250 relative to rod 240— one pair of nuts 241 are axially positioned immediately above and below upper plate 250, thereby maintaining the axial position of upper plate 250, and the other pair of nuts 241 are axially positioned immediately above and below the group of three baffles 260, thereby defining and limiting the axial position of baffles 260. For convenience purposes, nuts 241 may also be referred to as first, second, third, fourth, and fifth nuts 241 based on their axial position along rod 240 moving from lower end 240a to upper end 240b (i.e., the lower-most nut 241 is the first nut 241, the next nut 241 axially above the first nut 241 is the second nut 241, and so on).

Referring now to FIGS. 3-5, 7 and 8, each plate 250 is a cylindrical disc having a planar upper surface 251, a planar lower surface 252 parallel to upper surface 251, and a cylindrical radially outer surface 253 extending axially between surfaces 251, 252. In addition, each plate 250 has an axial thickness $T_{250}$ measured axially between surfaces 251, 252, and an outer radius $R_{250}$ measured radially from axes 205, 215, 235 to the outer surface 253.

Figure 7:
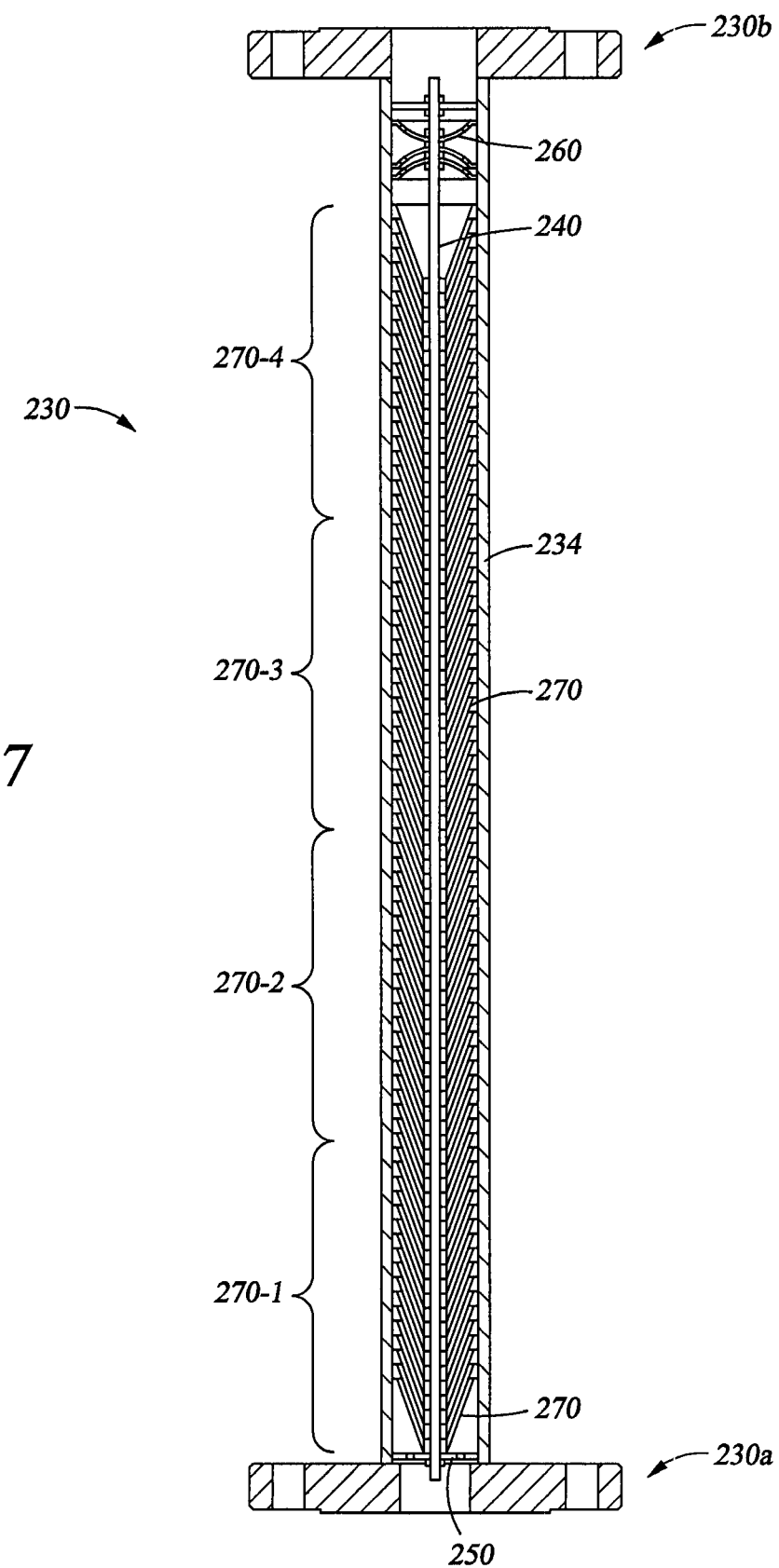
FIG. 7 is a cross-sectional view of the separator assembly of FIG. 3.
Figure 8:
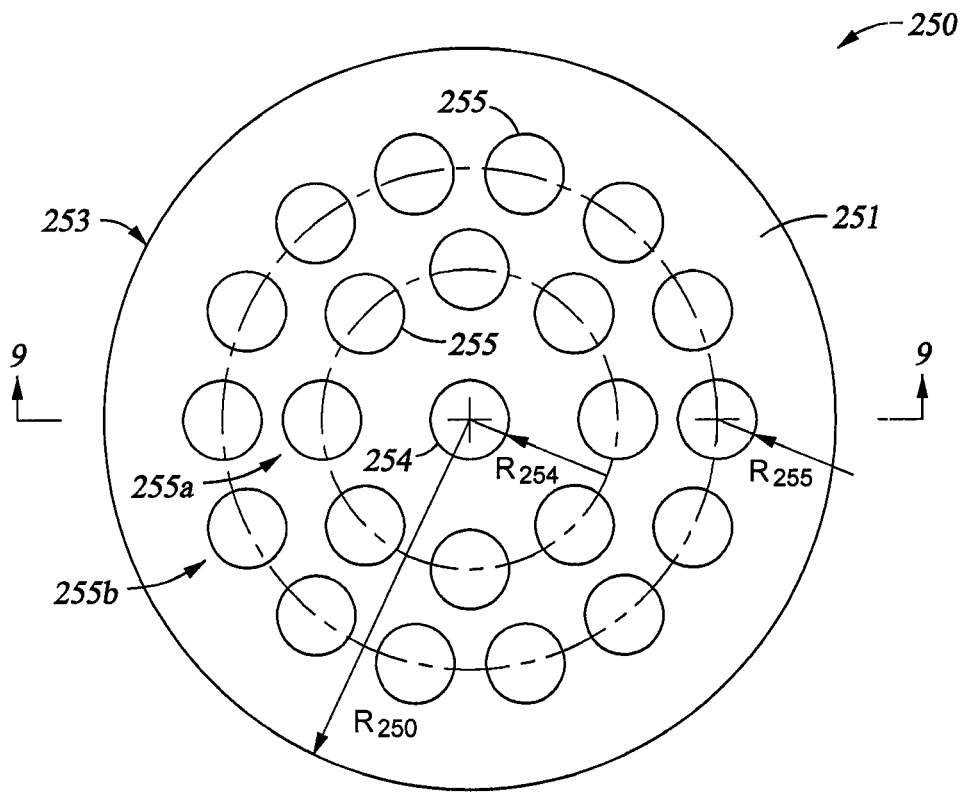
FIG. 8 is a top view of a plate of the fluid separator of FIG. 3.

Referring specifically to FIGS. 7 and 8, outer radius $R_{250}$ is preferably substantially the same or slightly less than the inner radius of conduit 234 such that outer surface 253 slidingly engages conduit 234 when plate 250 is coaxially disposed within conduit 234, and axial thickness $T_{250}$ preferably ranges from about 1/16 in. to about 1/4 in. In this embodiment, outer radius $R_{250}$, and hence the inner radius of conduit 234, is 1 1/4 in. and axial thickness $T_{250}$ is 1/8 in.

As best shown in FIGS. 7 and 8, each plate 250 includes a central throughbore 254 and a plurality of throughbores 255 radially positioned between central throughbore 254 and radially outer surface 253. Each bore 254, 255 extends axially through plate 250 from upper surface 251 to lower surface 252. In this embodiment, a first set of eight bores 255 are disposed at the same radial position and arranged in a first annular row 255a, and a second set of fourteen bores 255 are disposed at the same radial position and arranged in a second annular row 255b. Row 255a is radially positioned between central bore 254 and annular row 255b.

Referring still to FIGS. 7 and 8, central bore 254 has a radius $R_{254}$ and each bore 255 has a radius $R_{255}$. In this embodiment, each bore 255 has the same radius $R_{255}$. As best shown in FIGS. 4 and 5, central bore 254 slidingly receives rod 240, and thus, radius $R_{254}$ is preferably substantially the same or slightly less than the outer radius of rod 240. As previously described, support rod 240 has an outer radius $R_{240}$ that is preferably between 1/16 in. and 3/16 in., and thus, radius $R_{254}$ is preferably between 1/16 in. and 3/16 in. In this embodiment, radius $R_{240}$ is 1/8 in, and thus, radius $R_{254}$ is about 1/8 in. or slightly less than 1/8 in. Still further, radius $R_{255}$ of each bore 255 preferably ranges from about 1/16 in. to 3/16 in. In this embodiment, the radius $R_{255}$ of each bore 255 is 1/8 in.

As will be described in more detail below, throughbores 255 allow fluid within separator assembly 230 to flow axially through each plate 250. In particular, throughbores 255 in lower plate 250 allow unconditioned sample fluid 101, typically in a gaseous phase with some suspended particulate matter, to flow through inlet 231 into separator assembly 230 and allow contaminants 102, typically in a liquid phase, to flow axially downward through outlet 232 and out of separator assembly 230. Further, throughbores 255 in upper plate 250 allow conditioned sample fluid 103, typically in a gaseous phase, to flow through outlet 233 and out of separator assembly 230. Consequently, throughbores 255 in plates 250 may also be referred to as fluid ports or fluid orifices.

Referring again to FIGS. 3 and 4, in this embodiment, separator assembly 230 includes three baffles 260 axially positioned proximal upper end 230b between separating members 270 and upper plate 250. Baffles 260 axially spaced apart and are arranged one-above-the-other in a vertical or axial stack. For convenience purposes, the three baffles 260 may be referred to as the first, second, and third baffles 260 based on their order moving axially along rod 240 from lower end 240a to upper end 240b (i.e., the lower-most baffle 260 is the first baffle 260 and the upper-most baffle 260 is the third baffle 260).

As previously described, one nut 241 is axially positioned immediately below the lowermost or first baffle 260 and one nut 241 is positioned immediately above the upper most or third baffle 260, thereby limiting the axial movement and positions of baffles 260. In addition, one spacer 290 is axially positioned between each pair of adjacent baffles 260; spacers 290 maintain axial separation of baffles 260. In other words, axially adjacent baffles 260 do not touch or engage each other.

Referring now to FIGS. 3, 4, 9 and 10, each baffle 260 is a generally dome-shaped disc having a convex surface 261 and a concave surface 262 parallel to surface 261. In this embodiment, surfaces 261, 262 are spherical surfaces. Each baffle 260 also includes an annular lip or flange 263 along its entire outer periphery. Lip 263 defines a radially outermost cylindrical surface 264 on each baffle 260. As best shown in FIGS. 3 and 4, in this embodiment, first and second baffles 260 are each oriented with concave surface 262 facing downward, whereas third baffle 260 is oriented with concave surface 262 facing upwards and toward upper plate 250. Further, although first and second baffles 260 are axially spaced apart and do not directly engage each other, first and second baffles 260 are arranged in a nested configuration wherein first baffle 260 extends partially into the concave recess defined by concave surface 262 of second baffle 260.

Figure 9:
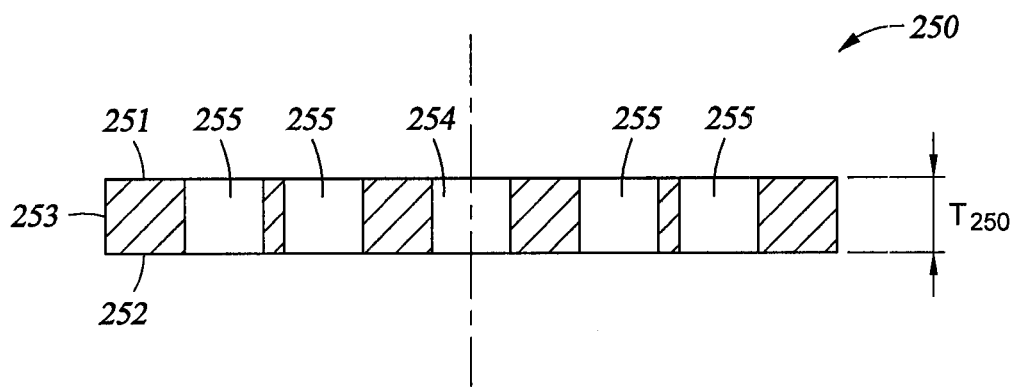
FIG. 9 is a cross-sectional view of the plate of FIG. 8 taken along section 8-8 of FIG. 8.
Figure 10:
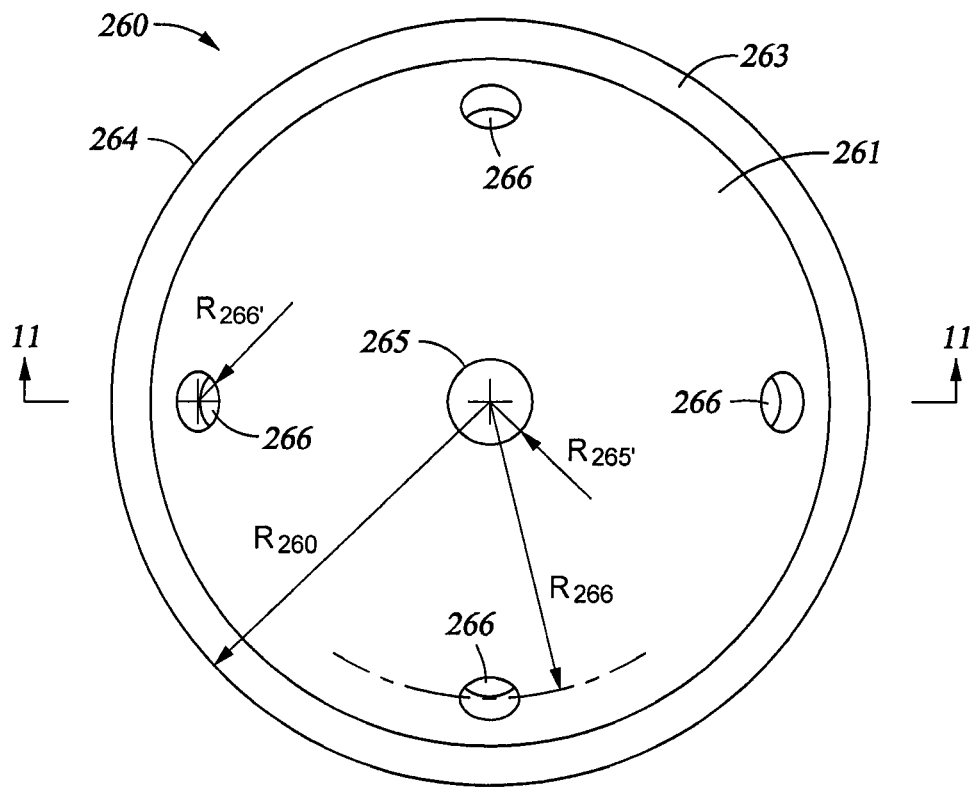
FIG. 10 is a top view of a baffle of the fluid separator of FIG. 3.

Referring specifically to FIGS. 9 and 10, each baffle 260 has an axial thickness $T_{260}$ measured axially between surfaces 261, 262, and an outer radius $R_{260}$ measured radially from axes 205, 215, 235 to the outer surface 264. Outer radius $R_{260}$ is preferably substantially the same or slightly less than the inner radius of conduit 234 such that outer surface 264 slidingly engages conduit 234 when baffle 260 is coaxially disposed within conduit 234, and axial thickness $T_{260}$ preferably ranges from about 1/16 in. to about 1/4 in. In this embodiment, outer radius $R_{260}$, and hence the inner radius of conduit 234, is 1 1/4 in. and axial thickness $T_{260}$ is 1/8 in.

Referring still to FIGS. 9 and 10, each baffle 260 includes a central throughbore 265. As best shown in FIGS. 3 and 4, central throughbore 265 of each baffle 260 slidingly receives rod 240. Thus, baffles 260 are coaxially disposed about rod 240 and coaxially disposed within conduit 234. In addition, each baffle 260 includes a plurality of throughbores 266 radially positioned between central throughbore 265 and annular flange 263. In this embodiment, four throughbores 266 are provided. However, in general, any suitable number of throughbores 266 may be provided. Each throughbore 266 is disposed at a radius $R_{266}$. In this embodiment, the radius $R_{266}$ of each throughbore 266 is the same. Throughbores 266 are preferably positioned in the radially outer 50% of baffle 260, and more preferably positioned in the radially outer 25% of baffle 260. In other words, radius $R_{266}$ of each throughbore 266 is preferably greater than 50% of outer radius $R_{260}$, and more preferably greater than 75% of outer radius $R_{260}$.

As previously described, in this embodiment, each baffle 260 includes four throughbores 266. In particular, throughbores 266 are uniformly angularly spaced about 90° apart. However, in other embodiments, the throughbores in the baffles (e.g., throughbores 266 in baffles 260) may be non-uniformly angularly spaced.

Baffles 260 are preferably coupled to rod 240 and angularly oriented relative to each other such that throughbores 266 on axially adjacent baffles 260 are disposed at different angular position relative to axes 205, 215, 235. For example, baffles 260 may be positioned on rod 240 without regard to the angular orientation of throughbores 266, in which case, throughbores 266 will most likely be positioned at random and different angular positions on adjacent baffles 260. As a result, the unconditioned sample fluid 101 flowing axially upward through separator assembly 230 is forced to change direction, and thus, take a more tortuous path to flow from bores 266 of one baffle 260 in route to bores 266 of the next axially adjacent baffle 260.

Referring still to FIGS. 9 and 10, central bore 265 has a radius $R_{265'}$ and each bore 266 has a radius $R_{266'}$. In this embodiment, each bore 266 has the same radius $R_{266'}$. As best shown in FIG. 4, central bore 265 slidingly receives rod 240, and thus, radius $R_{265'}$ is preferably substantially the same or slightly less than the outer radius of rod 240. As previously described, support rod 240 has an outer radius $R_{240}$ that is preferably between 1/16 in. and 3/16 in., and thus, radius $R_{265'}$ is preferably between 1/16 in. and 3/16 in. In this embodiment, radius $R_{240}$ is 1/8 in, and thus, radius $R_{265'}$ is about 1/8 in. or slightly less than 1/8 in. Still further, radius $R_{266'}$ of each bore 266 preferably ranges from 1/64 in. to 1/8 in. In this embodiment, the radius $R_{266'}$ of each bore 266 is 1/16 in.

As will be described in more detail below, throughbores 266 allow fluid within separator assembly 230 to flow axially through each baffle 260. In particular, throughbores 266 in baffles 260 allow unconditioned sample fluid 101 (or partially conditioned fluid sample), typically in a gaseous phase, to flow axially upward through each baffle 260 towards outlet 233 of separator assembly 230. Accordingly, throughbores 266 may also be referred to as gas orifices or ports. Further, the gaps and/or annulus radially positioned between radially outer surface 264 of each baffle 260 and conduit 234 allow contaminants 102, typically in a liquid phase, to drip and flow axially downward through each baffle 260 toward outlet 233. Accordingly, the gaps and/or annuli positioned radially between each baffle 260 and conduit 234 may be referred to as drain gaps.

Referring now to FIGS. 3 and 6, in this embodiment, separator assembly 230 includes a plurality of separating members 270 generally arranged one-above-the-other in a vertical or axial stack. The lowermost separator member 270 axially abuts and engages lower plate 250. In addition, one spacer 290 is axially positioned between each pair of adjacent separating members 270. Thus, nut 241 disposed immediately below lower plate 250 supports lower plate 250 as well as the plurality of separating members 270 and spacers 290 disposed between separating members 270. Spacers 290 maintain axial separation of separating members 270. In other words, axially separating members 270 do not touch or engage each other. The axial spacing between adjacent separating members 270 preferably ranges from 1/32 in. to 1/4 in. Spacers 290 are preferably sized to maintain the preferred axial separation of adjacent separating members 270.

Figure 11:
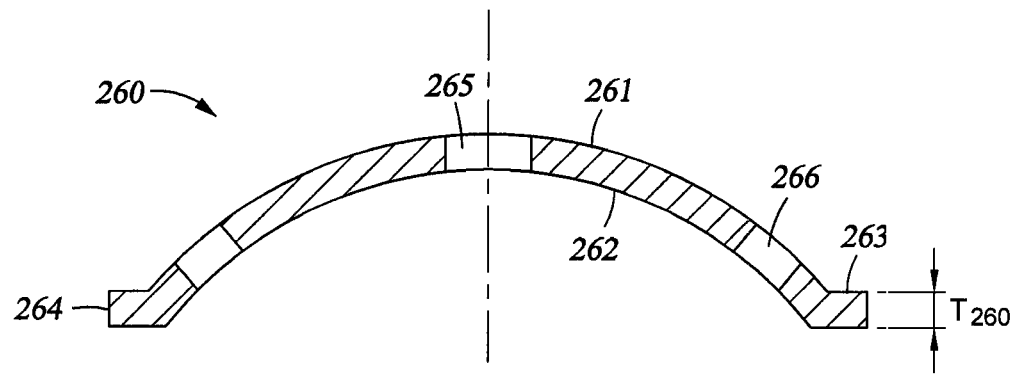
FIG. 11 is a cross-sectional view of the baffle of FIG. 10 taken along section 10-10 of FIG. 9.
Figure 12:
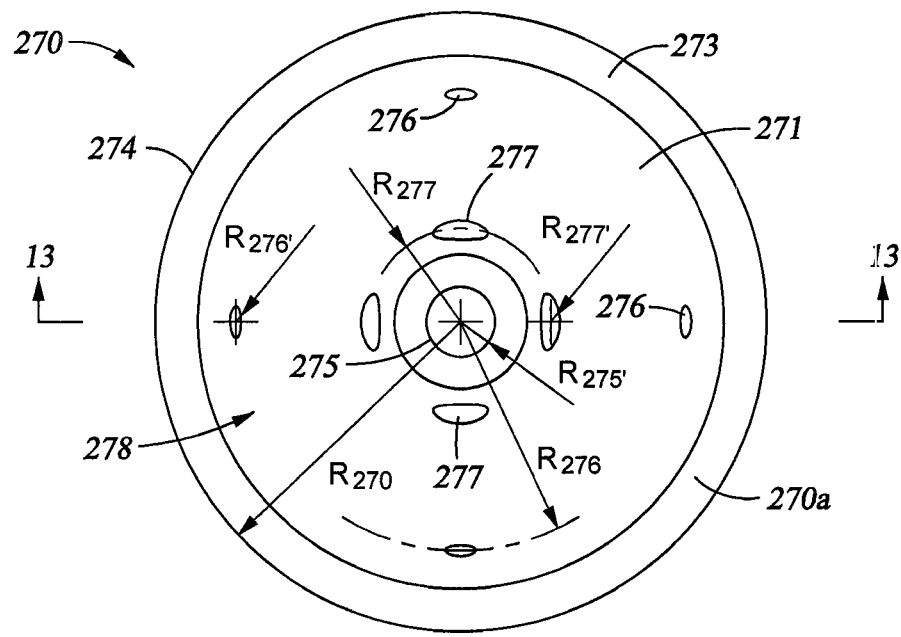
FIG. 12 is a top view of a separator member of the fluid separator of FIG. 3.
Figure 13:
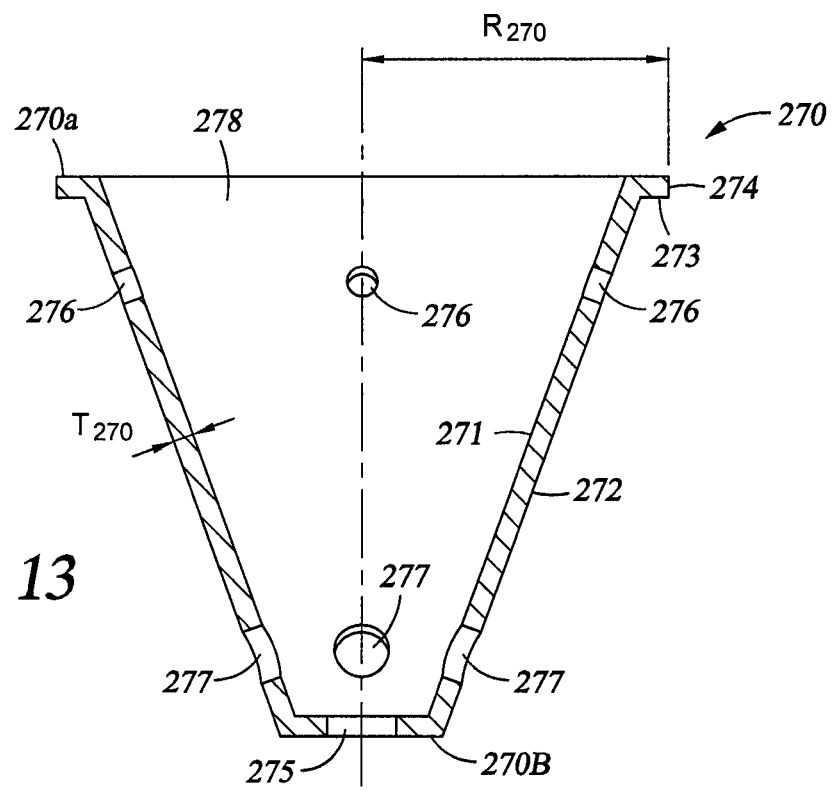
FIG. 13 is a cross-sectional view of the separator member of FIG. 12 taken along section 12-12 of FIG. 12.

Referring now to FIGS. 6, 11 and 12, each separator member 270 is generally an inverted cone extending between an upper end 270a and a lower end 270b. In addition, each separator member 270 has a frustoconical inner surface 271 and a frustoconical outer surface 272 parallel to inner surface 271. Upper end 270a includes an annular lip or flange 273 that extends along the entire outer periphery of upper end 270a. Lip 273 defines a radially outermost cylindrical surface 274 on each separator member 270. In this embodiment, lower end 270b is generally flat, however, in other embodiments, the lower end of each separating member (e.g., lower end 270b of each separator member 270) may be rounded, pointed, etc. Frustoconical inner surface 271 defines an inner cone-shaped cavity or recess 278 extending axially downward from the open upper end 270a. As best shown in FIGS. 3 and 6, with the exception of the lowermost separator member 270 that engages lower plate 250, each separator member 270 extends into recess 278 of the separator member 270 axially positioned immediately below it. Thus, separator members 270 may be described as being arranged in a nested configuration wherein each separator member 270 extends axially into recess 278 of an axially adjacent separator member 270.

Referring specifically to FIGS. 11 and 12, each separator member 270 has an axial thickness $T_{270}$ measured perpendicularly to surfaces 271, 272 and an outer radius $R_{270}$ measured radially from axes 205, 215, 235 to outer surface 274. Outer radius $R_{270}$ is preferably substantially the same or slightly less than the inner radius of conduit 234 such that outer surface 274 slidingly engages conduit 234 when separating members 270 are coaxially disposed within conduit 234, and axial thickness $T_{270}$ preferably ranges from about 1/16 in. to about 1/4 in. In this embodiment, outer radius $R_{270}$, and hence the inner radius of conduit 234, is 1 1/4 in. and axial thickness $T_{270}$ is 1/8 in.

Each separator member 270 also includes a central throughbore 275 at lower end 270b. As best shown in FIGS. 3 and 6, central throughbore 275 of each separator member 270 slidingly receives rod 240. Thus, separator members 270 are coaxially disposed about rod 240 and coaxially disposed within conduit 234. In addition, each separator member 270 includes at least one throughbore 276 proximal upper end 270a, and at least one throughbore 277 proximal lower end 270b. In general, each separator member 270 may include any suitable number of throughbores 276 and any suitable number of throughbores 277. Further, different separator members 270 in separator assembly 230 may have different numbers of throughbores 276 and/or throughbores 277. However, the number of throughbores 276 in each separator member 270 preferably ranges from one to four, and the number of throughbores 277 in each separator member 270 also preferably ranges from one to four. In the embodiment of separator member 270 shown in FIGS. 11 and 12, four throughbores 276 and four throughbores 277 are provided.

As will be described in more detail below, throughbores 276, 277 allow fluid within separator assembly 230 to flow axially through each separator member 270. In particular, throughbores 276 in separating members 270 allow unconditioned sample fluid 101 (or partially conditioned fluid sample), typically in a gaseous phase with some particulate matter, to flow axially upward through each separator member 270 towards outlet 233 of separator assembly 230. Accordingly, throughbores 276 may also be referred to as gas orifices or ports. Further, throughbores 277 in separating members 270 allow contaminants 102, typically in a liquid phase, to drip and flow axially downward through each separator member 270 towards outlet 233. Accordingly, throughbores 277 may also be referred to as drain orifices or ports.

Referring still to FIGS. 11 and 12, each throughbore 276 is disposed at a radius $R_{276}$ and each throughbore 277 is disposed at a radius $R_{277}$ that is less than radius $R_{276}$. In this embodiment, the radius $R_{276}$ of each throughbore 276 is the same and the radius $R_{277}$ of each throughbore 277 is the same. Since each separator member 270 has an inverted cone geometry, throughbores 276 proximal upper end 270a are radially positioned in the radially outer portion of each separator member 270, and throughbores 277 proximal lower end 270b are radially positioned in the radially inner portion of each separator member 270.

In this embodiment of separator member 270, the four throughbores 276 are uniformly circumferentially spaced about 90° apart, and the four throughbores 277 are uniformly circumferentially spaced about 90° apart. However, in general, the throughbores in one or more separating members (e.g., throughbores 276, 277 in separating members 270) may be non-uniformly circumferentially spaced.

Separating members 270 are preferably coupled to rod 240 and angularly oriented relative to each other such that throughbores 276 on axially adjacent separating members 270 are disposed at different angular position relative to axes 205, 215, 235. In other words, throughbores 276 of axially adjacent separating members 270 are preferably angularly offset or staggered. As a result, fluid (e.g., unconditioned sample fluid 101) flowing axially upward through separator assembly 230 is forced to change direction, and thus, take a more tortuous path when flowing from the bores 276 of one separator member 270 in route to the bores 276 of the next axially adjacent separator member 270.

Referring still to FIGS. 11 and 12, central bore 275 has a radius $R_{275'}$, each bore 276 has a radius $R_{276'}$, and each bore 277 has a radius $R_{277'}$ that is greater than radius $R_{276'}$. In this embodiment, the radius $R_{276'}$ of each bore 276 is the same, and the radius $R_{277'}$ of each bore 277 is the same. As best shown in FIG. 4, central bore 275 slidingly receives rod 240, and thus, radius $R_{275'}$ is preferably substantially the same or slightly less than the outer radius of rod 240. As previously described, support rod 240 has an outer radius $R_{240}$ that is preferably between 1/16 in. and 3/16 in., and thus, radius $R_{275'}$ is preferably between 1/16 in. and 3/16 in. In this embodiment, radius $R_{240}$ is 1/8 in, and thus, radius $R_{275'}$ is about 1/8 in. or slightly less than 1/8 in. Radius $R_{276'}$ of each bore 276 preferably ranges from 1/64 in. to 1/16 in., and radius $R_{277'}$ of each bore 277 preferably ranges from 1/16 in. to 3/16 in. As will be described in more detail below, radius $R_{276'}$ and radius $R_{277'}$ of gas orifices 276 and drain ports 277, respectively, may vary across different separator members 270 within separator assembly 230.

In general, the components of separator assembly 230 (e.g., conduit 234, plates 250, baffles 260, separating members 270, spacers 290, rod 240, etc.) may comprise any suitable materials such as metal(s) and metal alloys (e.g., aluminum, steel, etc.), non-metals (e.g., ceramics, polymers, etc.), composites, or combinations thereof. However, the components of separator assembly 230 preferably comprise rigid, durable materials that are capable of withstanding extended period of exposure to the relatively conditions (e.g., temperatures, corrosive effects, etc.) imposed by cooling fluid 221 and unconditioned sample fluid 101. Thus, in the embodiments described herein, the components of separator assembly 230 are made from stainless steel.

Referring briefly to FIG. 7, in this embodiment of separator assembly 230, different sets or groups of separating members 270 have different numbers of gas orifices 276, different numbers of drain ports 277, differently sized gas orifices 276, and differently sized drain ports 277 based on their relative axial positions within assembly 230. In particular, the plurality of separator members 270 in separator assembly 230 may be divided into different sets or groups 270-1, 270-2, 270-3, 270-4. In the embodiment of separator assembly 230 shown in FIG. 7, enerally preferred to have a lower dead volume and lower volumetric flow rate to o achieve a particular 70-3, 270-4 of twenty-five separator members 270. Groups 270-1, 270-2, 270-3, 270-4 are positioned one above the other starting at lower end 230a. Thus, group 270-1 is the lowermost set of twenty-five separator members 270, group 270-4 is the upper-most set of twenty-five separators 270, group 270-2 is positioned axially adjacent group 270-1, and group 270-3 is axially positioned between groups 270-2, 270-4.

Within a given group 270-1, 270-2, 270-3, 270-4, separator members 270 are identical. Thus, within a given group 270-1, 270-2, 270-3, 270-4, each separator 270 has the same number of gas orifices 276 and the same number of drain ports 277. Further, within a given group 270-1, 270-2, 270-3, 270-4, each gas orifice 276 has the same radius $R_{276'}$ and each drain port 277 has the same radius $R_{277'}$. However, separator members 270 in different groups 270-1, 270-2, 270-3, 270-4 are different. In particular, separator members 270 in different groups 270-1, 270-2, 270-3, 270-4 have different numbers of gas orifices 276 and different numbers of drain ports 277. For example, in the embodiment shown in FIG. 7, the number of gas orifices 276 and drain ports 277 generally decreases moving axially upward from group-to-group. Specifically, in group 270-1, each separator member 270 has four gas orifices 276 and four drain ports 277; in group 270-2, each separator member 270 has three gas orifices 276 and three drain ports 277; in group 270-3, each separator member 270 has two gas orifices 276 and two drain ports 277; and in group 270-4, each separator member 270 has one gas orifice 276 and two drain ports 277.

In this embodiment, gas orifices 276 of separators 270 in different groups 270-1, 270-2, 270-3, 270-4 have the same radii $R_{276'}$, and drain ports 277 of separators 270 in different groups 270-1, 270-2, 270-3, 270-4 have the same radii $R_{277'}$. In particular, in each group 270-1, 270-2, 270-3, 270-4, radius $R_{276'}$ of each gas orifice 276 is 1/16 in. and radius $R_{277'}$ of each drain port 277 is 1/16 in. However, in other embodiments, gas orifices 276 of separators 270 in different groups 270-1, 270-2, 270-3, 270-4 may have different radii $R_{276'}$, and/or drain ports 277 of separators 270 in different groups 270-1, 270-2, 270-3, 270-4 may have different radii $R_{277'}$. For example, the radius $R_{276'}$ of gas orifices 276 of separators 270 in different groups 270-1, 270-2, 270-3, 270-4 may decrease from group-to-group moving axially upward, and radius $R_{277'}$ of drain ports 277 of separators 270 in different groups 270-1, 270-2, 270-3, 270-4 may decrease from group-to-group moving axially upward.

Referring now to FIGS. 3-7, to assembly separator assembly 230, first nut 241 is threaded onto lower end 240a of support rod 240, and then plates 250, separating members 270, spacers 290, baffles 260, and remaining second, third, fourth, and fifth nuts 241 are coupled to rod 240 in order from the bottom up, one after the other. Plates 250, separating members 270, spacers 290, and baffles 260 slidingly engage rod 240, and thus, an axial force can be applied to these components to axially urge them along rod 240 from upper end 240b to lower end 240a. Alternatively, rod 240 may be positioned in a vertical orientation such that the weight of plates 250, separating members 270, spacers 290, and baffles 260 naturally urges them axially downward along rod 240 toward lower end 240a.

Once first nut 241 is threaded onto lower end 240a, upper end 240b of support rod 240 is axially inserted into central throughbore 254 of lower plate 250, and rod 240 is axially advanced through throughbore 254 until lower plate 250 axially abuts first nut 241 at lower end 240a. Next, upper end 240b of support rod 240 is axially inserted into central throughbore 275 of lower-most separator member 270, and rod 240 is axially advanced through throughbore 275 until lower end 270b axially abuts lower plate 250. Then, rod 240 is axially advanced through spacers 290 and central throughbore 275 of the remaining separating members 270 in an alternating fashion until all the separating members 270 are coupled to rod 240. As previously described, gas orifices 276 in axially adjacent separating members 270 are preferably positioned at different angular orientations. Neither rod 240 nor central throughbores 275 of separating members 270 are keyed, and thus, separating members 270 are free to rotate about axis 235 during assembly. As a result, during assembly, the angular orientation of gas orifices 276 of one separator member 270 relative to the angular orientation of the gas orifices 276 of every other separator member 270 is random. Consequently, the probability of two or more axially adjacent separating members 270 having gas orifices 276 with the same angular orientation is relatively low, and the probability of every separator member 270 having gas orifices 276 with the same angular orientation is extremely low.

As previously described, in the embodiment shown in FIGS. 3 and 7, the plurality of separating members 270 are arranged into groups 270-1, 270-2, 270-3, 270-4, where the number and radius $R_{276}$, of gas orifices 276 of each separating member 270 in the same, but the number and radius $R_{276'}$ of gas orifices 276 of separating members 270 in different groups are different. During assembly of separator assembly 230, special attention should be given to the order in which the separator members 270 are advanced onto rod 240 to achieve the desired arrangement of groups 270-1, 270-2, 270-3, 270-4. Specifically, separator members 270 designed and configured for use in group 270-1 should be placed on rod 240, before separator members 270 designed and configured for use in group 270-2; separator members 270 designed and configured for use in group 270-2 should be placed on rod 240, before separator members 270 designed and configured for use in group 270-3; and separator members 270 designed and configured for use in group 270-3 should be placed on rod 240, before separator members 270 designed and configured for use in group 270-4.

Referring still to FIGS. 3-7, and moving on with the remainder of the assembly process, after the final and upper-most separator member 270 is positioned on rod 240, second nut 241 is threaded onto upper end 240b, followed by axial insertion of upper end 240b into central throughbore 265 of first baffle 260, which is preferably oriented with concave surface 262 facing downward. Second nut 241 and first baffle 260 are axially advanced along rod 240 until second baffle 260 is positioned proximal, but axially spaced from, the upper-most separator member 270, and concave surface 262 axially abuts second nut 241. Accordingly, second nut 241 maintains the axial separation of first baffle 260 and the upper-most separator member 270. Next, two spacers 290, second baffle 260, and third baffle 260 are axially advanced onto rod 240 in an alternating fashion; second baffle 260 is preferably oriented with concave surface 262 facing downward similar to first baffle 260, and third baffle 260 is preferably oriented with concave surface 262 facing upward. Then, third nut 241 is threaded onto upper end 240b and advanced along rod 240 until it axially abuts third baffle 260. Second nut 241 and third nut 241 axially compress or squeeze baffles 260 and spacers 290 between baffles 260 together, thereby maintaining the axial position of baffles 260 and spacers 290 therebetween. Lastly, fourth nut 241 is threaded onto upper end 240b, upper end 240b is axially inserted and advanced through central throughbore 254 of upper plate 250, and fifth nut 241 is threaded onto upper end 240b. Fourth and fifth nuts 241 are positioned such that each axially abuts upper plate 250, thereby maintaining the axial position of upper plate 250.

Referring now to FIG. 3, fifth nut 241 is preferably axially positioned on rod 240 such that threaded upper end 240b extends axially upward from fifth nut 241. This threaded extension of rod 240 allows an extractor tool (not shown) having a counterbore with mating internal threads to be threaded onto upper end 240a to manipulate rod 240, plates 250, baffles 260, and separating members 270 coupled thereto. For example, once threaded to upper end 240b, the extractor tool may be used to pull rod 240, plates 250, baffles 260, and separating members 270 from conduit 234 for maintenance and/or cleaning operations, and insert rod 240, plates 250, baffles 260, and separating members 270 into conduit 234 following maintenance and/or cleaning operations. Accordingly, embodiments of fluid separator 200 enable removal of rod 240, plates 250, baffles 260, and separating members 270 axially for maintenance and/or cleaning operations without necessitating the removal of conduit 234 or insulating sleeve 210.

Referring back to FIG. 2, sample monitoring and control system 300 includes a plurality of temperature sensors, a plurality of flow control valves, and a plurality of valve actuators, which work together to monitor and control the conditioning of the sampled fluid within separator 200. The information acquired by system 300 in the field is communicated to a control room, by hardwire or wirelessly, where it may be monitored by a computer system and/or plant operations personnel. The control room may be on-site or remote from the processing operations. In response to the acquired information, the computer system and/or plant operations personnel may make various adjustments to the separation process via the control valves and valve actuators.

In this embodiment, system 300 includes a conditioned sample fluid temperature sensor 311, one cooling fluid inlet temperature sensor 314 for each cooling device 220 and cooling fluid inlet 213, one cooling fluid outlet temperature sensor 314 for outlet 214, and a plurality of additional cooling fluid temperature sensors 314 positioned in ports 222 of sleeve 210 between inlets 213 and outlet 214. Conditioned sample fluid temperature sensor 311 is positioned at or proximal outlet 233 of separator 200, and measures the temperature of conditioned sample fluid 103 at outlet 233. Each cooling fluid inlet temperature sensor 314 is positioned at or proximal one inlet 213 of separator 200, and measures the temperature of the cooling fluid 221 at that particular inlet 213. Further cooling fluid outlet temperature sensor 314 is positioned at or proximal cooling fluid outlet 214, and measures the temperature of cooling fluid 221 at outlet 214. The remaining cooling fluid temperature sensors 314 disposed in sensor ports 222 between inlets 213 and outlet 214 measure the temperature of cooling fluid 221 flowing through insulating chamber 216 at different axial positions along sleeve 210 and chamber 216.

Referring still to FIG. 2, in this embodiment, system 300 also includes one cooling fluid inlet control valve 321 and associated valve control actuator 331 for each cooling device 220, and a conditioned fluid outlet control valve 322 and associated valve control actuator 332. Valve control actuators 331, via valves 321, control the flow of cooling fluid 221 into cooling devices 220 and inlets 213 of separator 200. In particular, valves 321 are in an opened position, cooling fluid 221 flows to cooling devices 220 and inlets 213, however, when valves 321 are in a closed position, cooling fluid 221 is restricted and/or prevented from flowing to cooling devices 220 and inlets 213. Valve control actuators 331 actuate valves 321 between the opened position and the closed position. Further, as each valve 321 includes its own actuator 331, each valve 321 can be independently controlled. Each cooling device 220 also includes a cooling device actuator 341 that independently controls whether the particular cooling device 220 is on or off, as well as the degree of cooling power output by each cooling device 220.

Valve control actuator 332, via valve 322, controls the flow of conditioned fluid sample 103 through outlet 233 of separator 200. In particular, valve 322 is in an opened position, conditioned sample fluid 103 flows from separator 200 to the downstream equipment (e.g., analytical hardware), however, when valve 322 is in a closed position, conditioned sample fluid 103 is restricted and/or prevented from flowing through outlet 233 from separator 200 to the downstream equipment. Valve control actuator 332 actuates valves 322 between the opened position and the closed position. In general, each control actuators (e.g., actuators 331, 332, 341) may be any suitable type of actuator including, without limitation, electronic, hydraulic, or pneumatic actuators.

By employing the temperature sensors (e.g., temperature sensors 311, 314), valves (e.g., valves 321, 322), and actuators (e.g., actuators 331, 332, 341) previously described, system 300 is capable of acquiring, real-time, (a) the temperature of cooling fluid 221 at each inlet 213, at outlet 214, and at different axial positions along insulating chamber 216 between inlets 213 and outlet 214; (b) the temperature of conditioned sample fluid 103 at outlet 233; (c) the status and position of each valve 321, 322 (e.g., open, closed, etc.); and (d) the status of each cooling device 220 (e.g., on, off, etc.). In addition, by controlling valves 321 and cooling devices 220 with actuators 331, 341, respectively, system 300 is capable of controlling the temperature of cooling fluid 221 at inlets 213, which in turn allows system 300 to control the temperature of cooling fluid 221 within insulating chamber 216 and at outlet 214, as well as control the temperature of sample fluids 101, 103. Still further, by controlling valve 322 with actuator 332, system 300 is capable of controlling the flow of conditioned sample fluid 103 flowing from separator 200 to the downstream equipment.

As shown in FIG. 2, in this embodiment, valves 321, 322, associated actuators 331, 332, and condition sample fluid outlet temperature sensor 311 are disposed in a housing 360 coupled to upper end 200b of separator 200. Further, the cabling for temperature sensors 314 and actuators 341 is routed to housing 360. The information acquired with system 300 (i.e., the temperature of cooling fluid 221 at inlets 213, at outlet 214, and within insulating chamber 216; the status and position of valves 321, 322; the status and cooling power of cooling devices 220; and the temperature of conditioned sample fluid 103), is communicated from housing 360 to the control room, and condition sample fluid 103 is communicated from housing 360 to the downstream equipment.

Referring now to FIGS. 2-6, during sampling operations, one or more cooling devices 220 are turned on with actuator(s) 341, and valve 321 for each operating cooling device 220 is maintained in the opened position with actuator(s) 331. As a result, cooling fluid 221 flows through valve(s) 321 to cooling device(s) 220, where the temperature of cooling fluid 221 is reduced. The temperature of cooling fluid 221 at inlet(s) 213 is preferably between 38 and 42° F. Inlet temperature sensors 314 measure the temperature of cooling fluid 221 at inlets 213, and based on the temperature of cooling fluid 221 at inlets 213, additional cooling devices 220 may be turned on, an operating cooling device 220 maybe turned off, and/or the degree of cooling provided cooling devices 220 may be increased or decreased to achieve the desired temperature for cooling fluid 221 at inlets 213. Cooling fluid 221 is cooled by cooling devices 220 and pumped through inlets 213 into insulating chamber 216, and axially downward through insulating chamber 216 to outlet 214, where cooling fluid 221 exits separator 200. As cooling fluid 221 flows through insulating chamber 216, it comes into contact with conduit 234. Simultaneously, unconditioned decoke fluid sample 101 is pulled from a bulk decoke fluid stream. The bulk decoke fluid stream, and hence the unconditioned decoke fluid sample 101, typically has a temperature between 350 and 700° F. and is in a gaseous state with some suspended particulate matter. The unconditioned decoke fluid sample 101 enters inlet 101 at the lower end 230a of separator assembly 230 and flows through separator assembly 230. Thus, conduit 234 is in contact with both the relatively cold cooling fluid 221 and the relatively hot decoke fluid stream 101. As a result, heat transfer occurs across conduit 234. In particular, thermal energy in decoke fluid stream 101 is transferred across conduit 234 and into cooling fluid 221, thereby increasing the temperature of cooling fluid 221 as it moves axially downward through insulating chamber 216, and decreasing the temperature of decoke fluid stream 101 as it moves axially upward through separator assembly 230. In other words, the temperature of cooling fluid 221 is coldest at inlets 213, steadily increase moving axially downward through insulating chamber 216 toward outlet 214, and is warmest at outlet 214; and the temperature of decoke sample fluid 101 is greatest at inlet 231, decreases steadily moving axially upward through separator assembly 230, and is coolest at outlet 233. In this sense, separator 200 operates like a heat exchanger—moving thermal energy from decoke fluid stream 101 into cooling fluid 221. The temperature of cooling fluid 221 at different axial positions between inlets 213 and outlet 214 is measured with the remaining temperature sensors 314 in ports 222, and thus, the increase in temperature of cooling fluid 221 can be monitored and tracked as it progresses from inlet 213 to outlet 214.

Referring now to FIGS. 3 and 5, the unconditioned decoke fluid sample 101 enters inlet 101 at the lower end 230a of separator assembly 230 and migrates upward through separator assembly 230. Upon entry into separator assembly 230, unconditioned decoke fluid sample 101 first encounters lower plate 250. Within separator 200, unconditioned decoke fluid sample 101 has its maximum temperature at inlet 231. Lower plate 250, being in direct and/or indirect contact with conduit 234, has a temperature that is less than unconditioned decoke fluid sample 101 at inlet 231. As unconditioned decoke fluid 101 encounters lower plate 250, it is cooled as it contacts lower plate 250 and is forced to flow through bores 255 in lower plate 250. Further, due to the radius $R_{255}$ of bores 255, some of the relatively large particulate matter in unconditioned decoke sample fluid 101 is restricted and/or prevented from flowing through lower plate 250.

As best shown in FIGS. 3, 5, and 6, after passing through lower cold plate 250, unconditioned decoke sample fluid 101 encounters the plurality of separator members 270; unconditioned decoke sample fluid 101 first encounters separators 270 of group 270-1, followed by separators 270 of group 270-2, separators 270 of group 270-3, and finally separators 270 of group 270-4. In general, unconditioned decoke sample fluid 101 is free to flow through gas orifices 276 and/or drain ports 277 in separator members 270. However, due to the inverted cone geometry of each separator member 270, as unconditioned decoke sample fluid 101 moves axially upward and encounters the lower-most separator member 270, a substantial portion of unconditioned decoke sample fluid 101 is urged to move radially outward by frustoconical lower surface 272. As a result, the majority of unconditioned decoke sample fluid 101 is generally guided or funneled towards gas orifices 276. After passing through gas orifices 276 of the lower-most separator member 270, the unconditioned decoke sample fluid 101 primarily flows through gas orifices 276 of the remaining separator members 270 since the relatively hot unconditioned decoke sample fluid 101 inherently wants to rise axially upward, and sample fluid 101 exits gas orifices 276 at an axial location above drain ports 277 and below gas orifices 276 of the next successive separator member 270.

Similar to lower plate 250, the temperature of separator members 270 is less than the temperature of unconditioned decoke sample fluid 101. As sample fluid 101 flows across separator members 270, thermal energy is transferred from the relatively warmer sample fluid 101 to the relatively cooling device separator members 270, and the temperature of sample fluid 101 decreases. As the temperature of sample fluid 101 decreases, contaminants 102 (i.e., water and heavy hydrocarbons) begin to coalesce and form relatively heavy liquid droplets, which begin to drain and flow under the force of gravity downward along surfaces 271, 272 and through drain ports 277 in separating members 270. It should be appreciated that particulate matter in sample fluid 101 may become captured in such droplets and flow axially downward through drain ports 277 along with the droplets. Contaminants 102 flow along surfaces 271, 272 and through drain ports 277 to lower plate 250, and then flow axially downward through bores 255 in lower plate 250 and outlet 232 back into the bulk decoke fluid stream. However, as contaminants 102 coalesce and drain, the remaining unconditioned decoke sample fluid 101, which has been at least partially conditioned by the removal of some contaminants 102, continues to migrate upward through gas orifices 276.

Referring now to FIGS. 3, 4, and 6, after migrating upward in separator assembly 230 through separator members 270 via gas orifices 276, unconditioned decoke sample fluid 101 encounters baffles 260. As previously described, the temperature of cooling fluid 221 in insulating chamber 216, the temperature of separator assembly 230, and the temperature of unconditioned decoke sample fluid 101 is lowest proximal upper end 230b, baffles 260, and upper plate 250. In addition, since gas orifices 276 of axially adjacent separator members 270 are preferably disposed at different angular positions about axes 205, 215, 235, as unconditioned decoke sample fluid 101 migrates upward through separator assembly 230, it is forced to change directions along a tortuous path. As a result, the speed of unconditioned decoke sample fluid 101 gradually decreases and the pressure of unconditioned decoke sample fluid 101 gradually increases as it migrates through separator assembly 230 from inlet 231 to outlet 233. Thus, the pressure of unconditioned decoke sample fluid 101 is greatest proximal outlet 233 and upper end 230b, which is also the region at which the temperature of unconditioned decoke sample fluid 101 and separator assembly 230 are lowest. These conditions bring the molecules in unconditioned decoke sample fluid 101 closer together, thereby enhancing the potential for coalescence of any remaining contaminants 102. Thus, any contaminants in unconditioned decoke sample fluid 101 that did not coalesce on separator members 270 will coalesce as unconditioned decoke sample fluid 101 encounters baffles 260 and upper plate 250 and flows through gas orifices 266 and bores 255, respectively, resulting in the final transition of unconditioned decoke sample fluid 101 into conditioned sample fluid 103. Upon exiting bores 255 of upper plate 250, condition sample fluid 103 flows through outlet 233 of separator assembly 230.

The coalesced liquid contaminants 102 on the upper-most baffle 260 will tend to flow radially inward along surfaces 261, 262 drip onto the upper surface 261 of the middle baffle 260. The coalesced liquid contaminants 102 on the upper-most baffle 260 may also flow axially downward through any gaps between rod 240 and upper-most baffle 260 (i.e., through central bore 265). The coalesced liquid contaminants 102 on the lower two baffles 260 will tend to flow radially outward along surfaces 261, 262 and drain through any gaps between conduit 234 and radially outer surfaces 264 into recess 278 of the upper-most separator member 270. Small quantities of the coalesced liquid contaminants 102 may also drip through gas orifices 266 into recess 278 of the upper-most separator member 270. From recess 278 of upper-most separator member 270, liquid contaminants 102 drain axially downward as previously described.

In the manner previously described, unconditioned decoke sample fluid 101 is gradually transformed into conditioned sample fluid 103 by the gradual separation and removal of contaminants 102. Contaminants 102 are continuously separated and removed from unconditioned decoke sample fluid 101 as it migrates through separator assembly 230. Although sample fluid 101 is described as "unconditioned" as it moves through separator assembly 230, and sample fluid 103 is described as "conditioned" upon exiting separator assembly 230, it should be appreciated that sample fluid 101 is gradually conditioned along its entire migration through separator assembly 230, and is at its most "conditioned" state upon exiting separator assembly 230 via outlet 233.

Referring now to FIG. 2, as previously described, system 300 acquires real-time information relating to (a) the temperature of cooling fluid 221 at each inlet 213, outlet 214, and at different axial positions within insulating chamber 216; (b) the temperature of conditioned sample fluid 103 at outlet 233; (c) the status and position of each valve 321, 322 (e.g., open, closed, etc.); and (d) the status of each cooling device 220 (e.g., on, off, etc.). In addition, by controlling valves 321 and cooling devices 220 with actuators 331, 341, respectively, system 300 is capable of controlling the temperature of cooling fluid 221 at inlets 213, which in turn allows system 300 to control the temperature of cooling fluid 221 within insulating chamber 216 and outlet 214, as well as control the temperature of sample fluids 101, 103. Still further, by controlling valve 322 with actuator 332, system 300 is capable of controlling the flow of conditioned sample fluid 103 flowing from separator 200 to the downstream equipment. Further, as previously described, the separation and removal of contaminants 102 from unconditioned decoke sample fluid 101 results from the cooling of unconditioned sample fluid 101, increasing the pressure of unconditioned sample fluid 101, and the coalescence of contaminants 102 into liquid droplets. Accordingly, the temperature of unconditioned decoke sample fluid 101 as it migrates through separator assembly 230 is an important factor in the separation process—if the temperature of unconditioned decoke sample fluid 101 is not sufficiently decreased in separator assembly 230, then there may not be adequate separation and removal of contaminants 102. Without sufficient separation and removal of contaminants 102, equipment downstream of separator assembly 230 may be fouled and/or damaged.

The temperature of cooling fluid 221 at inlets 213 is preferably maintained between 38 and 42° F. This temperature range for cooling fluid 221 results in sufficient heat transfer from unconditioned sample fluid 101 to achieve an acceptable temperature for unconditioned sample fluid 101 (i.e., a temperature sufficiently low to achieve the desired separation and removal of contaminants 102). In particular, a cooling fluid inlet temperature between 38 and 42° F. results in a conditioned decoke sample fluid outlet temperature between 60 and 90° F. If the temperature of cooling fluid 221 at inlets 213, as measured by cooling fluid inlet temperature sensors 314, is too low, the degree of cooling provided by cooling devices 221 may be decreased via actuators 341 and/or one cooling device 221 may be completely turned off via its actuator 341. On the other hand, if the temperature of cooling fluid 221 at inlets 213, as measured by cooling fluid inlet temperature sensors 314, is too high, the degree of cooling provided by cooling devices 221 may be increased via actuators 341 and/or one or more additional cooling device(s) 221 may be turned on via its actuator 341. In some instances, the temperature of unconditioned fluid sample 101 and conditioned fluid sample 103 may still be too high. For example, the temperature of the bulk decoke fluid stream may unexpectedly spike, all cooling devices 221 may be operating at maximum capacity but still cannot achieve the preferred 38 and 42° F. cooling fluid inlet temperature, etc. If the temperature of conditioned sample fluid 103 exiting separator 200, as measured by sensor 311, is sufficiently high, such that an insufficient quantity of contaminants 102 were separated and removed, then system 300 can actuate valve 322 to the closed position with actuator 332, thereby restricting and/or preventing conditioned sample fluid 103 from flowing to downstream equipment.

Referring still to FIG. 2, in many analytical devices that measure ethylene and/or propylene yields from a conditioned decoke sample fluid (e.g., sample fluid 103), the measured yields (e.g., ethylene and/or propylene CC per minute) are often slightly different than the actual yields in the cracking furnace. Specifically, as the temperature of the sample gas exiting the chamber varies, the measured analyte value will change. If the fluid separator is operating at a temperature below set point, then the efficiency of the fluid separator has increased, thus resulting in the removal of additional heavy hydrocarbons or other possible impurities, such as water. The result is a volumetric increase in the measured analyte as reported by the process analyzer, which in this case is ethylene and/or propylene. In contrast, if the fluid separator is operating at a temperature above set point, then additional heavy hydrocarbons or other possible impurities, such as water will make up part of the overall sample to be measured by the process analyzer. Allowing the heavy hydrocarbons or impurities to exit the fluid sampler results in a volumetric decrease of the measured analyte, as reported by the gas chromatograph. In general, as the temperature of the conditioned decoke sample fluid 103 increases, the measured ethylene and/or propylene yields decreases, even though the actual ethylene and/or propylene yields in the furnace may not have changed at all. To date, it is believe that this phenomenon has not been recognized or accounted for by plant operators, probably due in part to the fact that most conventional sampling and conditioning devices do not measure or track the temperature of the conditioned decoke sample fluid temperature exiting the conditioning device. However, embodiments described herein offer the potential to enable plant operators to account for such differences between the measured ethylene and/or propylene yields and the actual yields in the furnace. In particular, it is believed that for every 1° F. increase in the temperature of conditioned decoke sample fluid 103 measured with sensor 311 at outlet 233, the measured ethylene and/or propylene yields increase by 0.1% to 0.3%, and more specifically increase by 0.2%; and for every 1° F. decrease in the temperature of conditioned decoke sample fluid 103 measured with sensor 311 at outlet 233, the measured ethylene and/or propylene yields decrease by 0.1% to 0.3%, and more specifically decrease by 0.2%. Accordingly, by measuring and tracking the temperature of conditioned decoke fluid sample 103 with system 300, plant operators can utilize these correlations to correct the measured yields.

Embodiments described herein offer the potential for several improvements over existing sampling and conditioning devices. For example, embodiments described herein provide decreased dead volume as compared most conventional sampling and conditioning devices. In general, the dead volume in a sampling and conditioning device refers to the total volume of empty space within a separating device (e.g., total empty space within conduit 234 of separator assembly 230). The relationship between the lag time (i.e., time for a particular sample to flow through the device), the volumetric flow rate of the sampled fluid through the device, and the dead volume of the device is as follows:

Lag Time~Dead Volume/Volumetric Flow Rate

Typically, the desired lag time is specified by the plant operators. For a given lag time, as dead volume increases, the volumetric flow rate of the sampled fluid through the device increases. However, without being limited by this or any particular theory, as the volumetric flow rate of the sampled fluid through the device increases, the separating efficiency and capacity of the device decreases (i.e., lower volumetric flow rate results in high pressure and more time within the device for cooling and coalescence). Consequently, it is generally preferred to have a lower dead volume and lower volumetric flow rate to achieve a particular lag time. In conventional sampling and conditioning device utilizing a series of steel mesh pads within a fluid conduit or pipe, the total dead volume is typically on the order of about three liters (3 L). However, for a similarly sized device in accordance with embodiments described herein, the total dead volume is on the order of about one and a half liters (1.5 L).

In addition to decreased dead volume compared to similarly sized conventional sampling and conditioning devices, embodiments described herein provide increased surface area for coalescence of the contaminants. Without being limited by this or any particular theory, the greater the available surface area in the sampling and conditioning device, the greater the coalescence and the greater the separation efficiency. The total surface area of the steel mesh pads provided in most conventional devices is about 144 in.$^2$. However, the components of a similarly sized device in accordance with the principles described herein (e.g., separator members, baffles, plates, etc.) provide a total surface area of about 1,884 in.$^2$ As previously described, maintenance and cleaning of most conventional sampling and conditioning devices require a complete removal of the device from the upstream and downstream conduits and removal of the steel mesh pads one-by-one. However, embodiments described herein offer the potential for easier access and maintenance. In particular, outlet 233 may be accessed by decoupling upper flange 203 from the adjacent hardware. An extractor tool may then be threaded onto upper end 240b of rod 240, and used to pull rod 240 and plates 250, baffles 260, spacers 290, and separator members 270 coupled thereto out of conduit 234. Once removed from conduit 234, rod 240 and plates 250, baffles 260, spacers 290, and separator members 270 may be inspected, cleaned, repaired, replaced, or combinations thereof, and then reinserted into conduit 234 on rod 240.

Referring still to FIG. 2, unlike most conventional sampling and conditioning devices that provide no insight into the sample temperature, the status of the sampling and conditioning device, or the temperature of the cooling fluid, embodiments described monitor and track the temperature of cooling fluid at various points, the temperature of conditioned sample fluid, the status of each cooling device, and the status of various valves controlling cooling fluid flow and conditioned sample fluid flow. In addition, by controlling such valves and cooling devices, embodiments described herein enable control of the temperature of cooling fluid and the sample fluid.

Although embodiments shown and described herein are discussed in terms of conditioning a decoke fluid sample from a hydrocarbon cracking operation to determine ethylene and/or propylene yields, in general, embodiments described herein may be used to condition other fluid samples In particular, embodiments of system 100 may be used where high moisture content, heavy hydrocarbons, particulate matter, and/or combinations thereof may be present in the unconditioned fluid sample and need to be removed prior to analysis. For example, embodiments described herein may be used to remove "green oil" from recycle gas or on a furnace decoke header to remove water and heavy particulates.

While preferred embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, the relative dimensions of various parts, the materials from which the various parts are made, and other parameters can be varied. Accordingly, the scope of protection is not limited to the embodiments described herein, but is only limited by the claims that follow, the scope of which shall include all equivalents of the subject matter of the claims.

What is claimed is:

1. A fluid sampling system comprising:
   a fluid separator including
      an insulating sleeve,
      a separator assembly disposed within and spaced radially inward with respect to the insulating sleeve to form an insulating chamber in an annular space between the insulting sleeve and separator assembly,
      a cooling device in fluid communication with the insulating chamber, wherein the separator assembly includes a conduit and a separator member within the conduit, and
      a baffle comprising a generally dome-shaped disc including a convex surface.

2. The fluid sampling system of claim 1, further comprising a plurality of separator members, wherein the separator members are stacked within the conduit.

3. The fluid sampling system of claim 2, wherein the separator members comprise a frustoconically-shaped plate and wherein the separator members are nested within other separator members.

4. The fluid sampling system of claim 3, wherein each separator member includes a gas orifice and a drain port.

5. The fluid sampling system of claim 4, wherein the gas orifice of each separator member is disposed at a different angular orientation than the gas orifice of each axially adjacent separator member.

6. The fluid sampling system of claim 4, wherein some of the separator members include additional gas orifices and drain ports and wherein some of the gas orifices and drain ports are of a different size relative to other of the gas orifices and drain ports.

7. The fluid sampling system of claim 1, further comprising a plurality of baffles and wherein the baffles are arranged one-above-the other within the conduit.

8. The fluid sampling system of claim 7, wherein each baffle includes a gas orifice.

9. The fluid sampling system of claim 8, wherein the baffles are oriented such that some of the convex surfaces face different directions.

10. The fluid sampling system of claim 1, further comprising a lower plate and an upper plate within the conduit, each plate including through bores.

11. The fluid sampling system of claim 1, wherein the insulating chamber includes an inlet and an outlet.

12. The fluid sampling system of claim 1, wherein the insulating sleeve includes a port configured to receive a sensor.

13. The fluid sampling system of claim 1, further comprising a valve in fluid communication with the separator assembly.

14. The fluid sampling system of claim 1, wherein the separator assembly further comprises fluid ports at its ends.

15. A fluid sampling system comprising:
   a fluid separator including
      an insulating sleeve, and
      a separator assembly disposed within and spaced radially inward with respect to the insulating sleeve, and including a conduit and a plurality of frustoconically-shaped separator members nested within the conduit, wherein each of the separator members includes a gas orifice and a drain port and wherein each of the gas orifices is disposed at a different angular orientation than the gas orifice of axially adjacent separator members.

16. The fluid sampling system of claim 15, wherein some of the separator members include additional gas orifices and drain ports and wherein some of the gas orifices and drain ports are of a different size relative to other of the gas orifices and drain ports.

17. The fluid sampling system of claim 15, wherein the insulating sleeve includes a port configured to receive a sensor.

18. A fluid sampling system comprising:
   a fluid separator including
      an insulating sleeve,
      a separator assembly disposed within and spaced radially inward with respect to the insulating sleeve, and including a conduit and a separator member within the conduit, and
      a plurality of dome-shaped baffles each including a convex surface and a gas orifice, arranged one-above-the other within the conduit, and oriented such that some of the convex surfaces face different directions.

19. The fluid sampling system of claim 18, wherein the insulating sleeve includes a port configured to receive a sensor.

* * * * *